United States Patent [19]
Gibson

[11] Patent Number: 6,047,513
[45] Date of Patent: Apr. 11, 2000

[54] STEEL CONSTRUCTION SYSTEM

[76] Inventor: J.W. Gibson, 146 Glassboro Dr., Oak Ridge, Tenn. 37830

[21] Appl. No.: 09/060,975

[22] Filed: Apr. 15, 1998

[51] Int. Cl.[7] ............................................. E04B 1/19
[52] U.S. Cl. .......................... 52/646; 52/640; 52/643; 52/645; 52/655.1; 52/690; 52/691; 52/712; 52/93.1; 52/93.2; 52/94
[58] Field of Search .......................... 52/690, 691, 639, 52/640, 641, 643, 645, 646, 655.1, 656.9, 712, 713, 93.1, 93.2, 94

[56] References Cited

U.S. PATENT DOCUMENTS

| | | |
|---|---|---|
| 1,392,070 | 9/1921 | Maiers . |
| 2,638,637 | 5/1953 | Kump, Jr. . |
| 2,638,643 | 5/1953 | Olson . |
| 2,840,014 | 6/1958 | Wadsworth et al. ................. 52/639 |
| 2,931,129 | 4/1960 | Boniface . |
| 2,982,055 | 5/1961 | Thompson . |
| 3,229,333 | 1/1966 | Hillesheim et al. . |
| 3,423,898 | 1/1969 | Tracy et al. ........................ 52/713 |
| 3,596,941 | 8/1971 | Tracy ................................. 52/713 X |
| 3,946,532 | 3/1976 | Gilb . |
| 3,985,459 | 10/1976 | Gilb . |
| 4,003,179 | 1/1977 | Gilb . |
| 4,007,573 | 2/1977 | Gilb . |
| 4,050,210 | 9/1977 | Gilb . |
| 4,069,635 | 1/1978 | Gilb . |
| 4,104,843 | 8/1978 | Gilb . |
| 4,106,257 | 8/1978 | Gilb . |
| 4,148,164 | 4/1979 | Humphrey ........................... 52/712 X |
| 4,230,416 | 10/1980 | Gilb . |
| 4,335,555 | 6/1982 | Southerland et al. . |
| 4,389,829 | 6/1983 | Murphy . |
| 4,410,294 | 10/1983 | Gilb et al. . |
| 4,411,547 | 10/1983 | Johnson . |
| 4,414,787 | 11/1983 | Kappen ............................... 52/639 X |
| 4,423,977 | 1/1984 | Gilb . |
| 4,449,335 | 5/1984 | Fahey ................................. 52/713 X |
| 4,551,957 | 11/1985 | Madray . |
| 4,620,397 | 11/1986 | Simpson et al. . |
| 4,688,358 | 8/1987 | Madray . |
| 4,697,393 | 10/1987 | Madray . |
| 4,717,279 | 1/1988 | Commins . |
| 4,720,957 | 1/1988 | Madray . |
| 4,756,133 | 7/1988 | Madray . |
| 4,817,359 | 4/1989 | Colonias . |
| 4,890,436 | 1/1990 | Colonias . |
| 4,897,979 | 2/1990 | Colonias . |
| 4,932,173 | 6/1990 | Commins . |

(List continued on next page.)

FOREIGN PATENT DOCUMENTS

| | | | |
|---|---|---|---|
| 1-219237 | 9/1989 | Japan ........................... 52/639 |
| 3-194053 | 8/1991 | Japan ........................... 52/690 |

OTHER PUBLICATIONS

Simpson Strong–Tie Company, Inc., Catalog C–94S–3, Jul. 1994.

Simpson Strong–Tie Company, Inc., Catalog C–95H–1, Jan. 1995.

*Primary Examiner*—Laura A. Callo
*Attorney, Agent, or Firm*—Luedeka, Neely & Graham, P.C.

[57] ABSTRACT

A construction system for building a steel frame using steel members. Rafters form a roof portion of the steel frame, and a ceiling joist having two ends forms a ceiling portion of the steel frame. Compression webs and tension webs, disposed between the rafters and the ceiling joists, distribute the load between the rafters and the ceiling joists. The tension webs are disposed between the rafters, the ceiling joists, and the compression webs, and inhibit distortion of the roof. A peak bracket connects two rafters and a compression web together. Eave brackets connect the two unconnected ends of the two connected rafters to the ends of the ceiling joist, such that each end of the ceiling joist aligns with one of the unconnected ends of the two connected rafters. Compression brackets connect the compression webs to the ceiling joist. A center bracket connects two of the tension webs and one of the compression webs to the ceiling joist. Channel brackets connect one of the tension webs and one of the compression webs to one of the rafters and the ceiling joist.

57 Claims, 23 Drawing Sheets

U.S. PATENT DOCUMENTS

| | | |
|---|---|---|
| 5,042,217 | 8/1991 | Bugbee et al. . |
| 5,109,646 | 5/1992 | Colonias et al. . |
| 5,341,619 | 8/1994 | Dunagen et al. . |
| 5,426,822 | 6/1995 | Weir ........................................ 52/640 X |
| 5,457,927 | 10/1995 | Pellock et al. . |
| 5,577,353 | 11/1996 | Simpson . |
| 5,890,339 | 4/1999 | Willis ........................................ 52/640 |

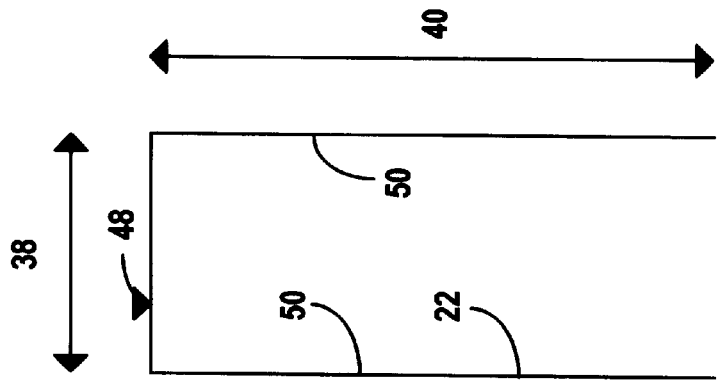
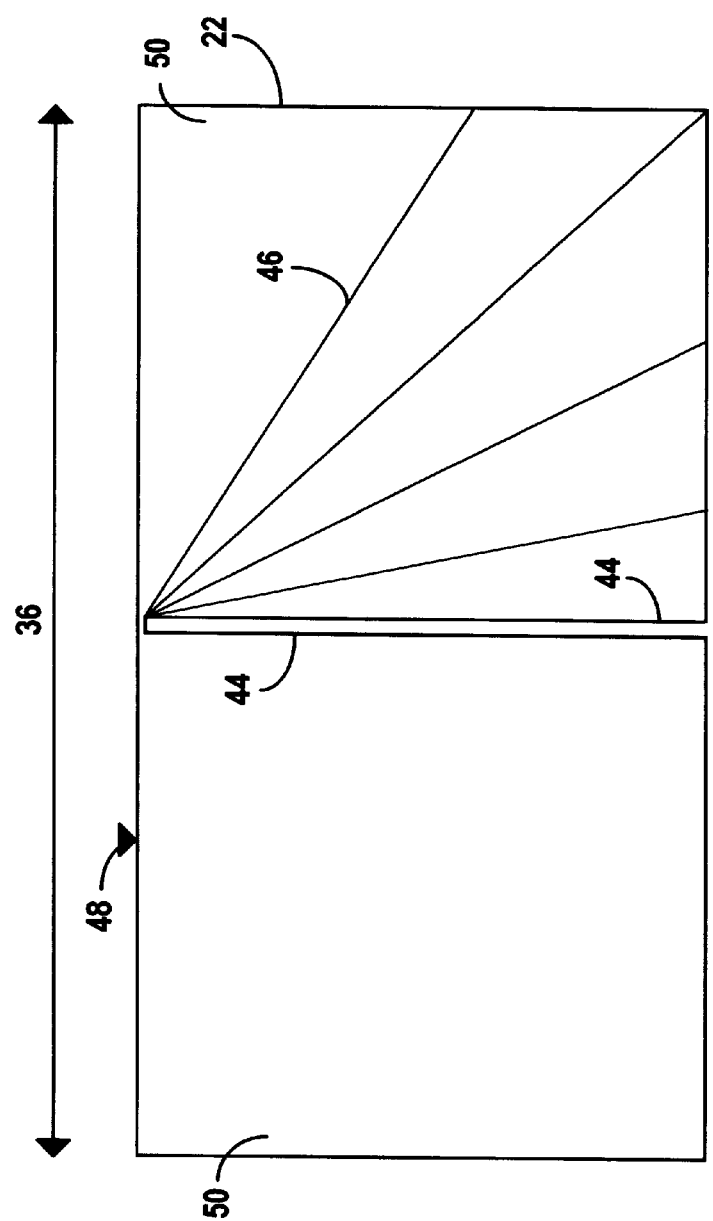

STEEL CONSTRUCTION SYSTEM

FIELD

This invention relates to steel construction systems. More particularly the invention relates to systems for connecting steel construction members, including rafters, webs, joists, and studs.

BACKGROUND

Construction systems using steel members instead of traditional wood members tend to be preferred for many building applications throughout the world. There are many different reasons why this is so. The steel members tend to be lighter than their wood counterparts, thus reducing the cost of shipping the members. Further, the structures built from the steel members will not be as heavy, thus reducing some loading concerns.

Steel members are also stronger than their wood counterparts. Thus, a smaller steel member can be used to replace a larger wood member, thus reducing the size of the support structure. Additionally, structures that would not be possible to build with wood members can be built with steel members, because the steel members have the strength sufficient for the design. In addition, steel members are available in virtually any length required, whereas there is a limit to the length of the wood members available. This also allows greater freedom in design when using steel members than that allowed by wood members.

In many areas of the world, steel members are more readily available than wood members, due to the scarcity of wood in those areas, and other factors. This and other factors tends to make the steel members less expensive than comparable wood members. Steel members may also be more durable and last longer than wood members, due to steel's resistance to things such as infestation and rot. Steel may also be more resistant to other environmental factors, which may also lengthen the useful life of a structure constructed with steel members. Further, steel construction systems can typically be assembled in less time than that required for wood member construction. In addition, less training is often required to assemble steel members into a frame, than is required to assemble wood members into a comparable frame.

Unfortunately, steel construction systems typically require a great number of different parts, including members and connectors. This is due to the large number of different configurations which are desired. Thus, steel construction systems typically require many different parts, each specifically adapted to a specific structure design and configuration.

What is needed therefore, is a construction system that requires relatively fewer parts, yet is adaptable to different structure designs and configurations. Further, such a system is needed which further simplifies the task of properly assembling the steel members into the frame.

SUMMARY

The above and other needs are met by a construction system for building a steel frame using steel members. Rafters formed of the steel members form a roof portion of the steel frame. A ceiling joist having two ends, also formed of the steel members, forms a ceiling portion of the steel frame. Compression webs and tension webs are also formed of the steel members, where the compression webs are disposed between the rafters and the ceiling joists, and distribute the load between the rafters and the ceiling joists. The tension webs are disposed between the rafters, the ceiling joists, and the compression webs, and inhibit distortion of the roof.

A unitary peak bracket connects two rafters at a variable roof pitch to a compression web. The peak bracket connects to three outside surfaces on each of the two rafters, and on two outside surfaces of the compression web. Each of the two connected rafters thereby has a connected end and an unconnected end. The peak bracket has a length, width, and height, and a spine with four overlapping flaps adjacent the spine. The four flaps are disposed at ninety degree angles from the spine, such that the four flaps and the spine have a cross-section generally resembling a U shape.

The spine is bendable to a variable degree at a position between the four flaps. At least one of the four flaps has alignment means on it, that are calibrated in units that indicate the variable degree at which the spine is bent. The spine has a predetermined number of holes in it, and each flap has at least eight holes in it. The eight holes in each flap are disposed such that four holes in each flap align with the compression web and one of the two connected rafters.

The peak bracket reduces the need for many different parts because it is bendable. Thus, the peak bracket can be bent to fit many different roof pitches. Further, the alignment means on the flap of the peak bracket allows it to be quickly bent to the proper roof pitch, thus automatically aligning the rafters to which it will be connected to the proper angle. This simplifies the construction of the steel frame. Further, the U shape of the peak bracket allows it to receive rafters of any height, as the rafters can extend out the open end of the U shaped peak bracket. In addition, the spine can be fastened to the rafters through the holes in the spine, thereby greatly increasing the strength of the joint.

Eave brackets connect the two unconnected ends of the two connected rafters to the ends of the ceiling joist, such that each end of the ceiling joist aligns with one of the unconnected ends of the two connected rafters. The eave brackets have a length, width, and height, and also have a spine with four flaps adjacent the spine. The four flaps are disposed at ninety degree angles from the spine, such that the four flaps and the spine have a cross-section generally resembling a U shape. The spine is bendable to a variable degree at a position between the four flaps. At least one of the four flaps has alignment means on it, the alignment means calibrated in units that indicate the variable degree at which the spine is bent. The spine also has a predetermined number of holes in it. Each flap has at least four holes in it, with the four holes in each flap disposed such that the four holes in each flap align with one of the ceiling joist and one of the two connected rafters.

The eave brackets allow the rafters and joists to be connected such that neither the ends of the rafters nor the ends of the joist leave an unfinished end, but are capped at the ends by the eave brackets. This provides a clean appearance and simplifies the construction of soffits under the ceiling joist. Further, the U shape of the eave bracket allows it to receive rafters and joists of any height, as the rafters and joists can extend out the open end of the U shaped eave bracket.

Compression brackets connect the compression webs to the ceiling joist. The compression brackets have a length, width, and height, and also have a spine with two flaps adjacent the spine. The two flaps are disposed at ninety degree angles from the spine, such that the two flaps and the spine have a cross-section generally resembling a U shape.

The spine has a predetermined number of holes in it, and each flap has at least eight holes in it. The eight holes in each flap are disposed such that four holes in each flap align with each of the connected compression web and the ceiling joist.

The compression brackets allow the compression webs to be connected to the ceiling joist in a manner such that the compression web does not have to overlie, or scab, the ceiling joist. This allows more of the steel frames to be stored or transported in a given area, because the compression web and the ceiling joist are within the same plane. Thus, the steel frame is only the thickness of one member instead of the thickness of two members. In addition, and also because the compression web and the ceiling joist are in the same plane, the load on the steel frame is more properly distributed throughout the steel frame, and the steel frame does not tend to torque under load. Further, the U shape of the compression brackets allows them to receive compression webs and ceiling joists of any height, as the compression webs and ceiling joists can extend out the open end of the U shaped compression brackets. In addition, the spine can be fastened to the ceiling joist through the holes in the spine, thereby greatly increasing the strength of the joint.

A center bracket connects two of the tension webs and one of the compression webs to the ceiling joist. The center bracket has a length, width, and height, and also has a spine with two flaps adjacent the spine. The two flaps are disposed at ninety degree angles from the spine, such that the two flaps and the spine have a cross-section generally resembling a U shape. The spine has a predetermined number holes in it, and each flap has at least sixteen holes in it. The sixteen holes in each flap are disposed such that at least four holes in each flap align with each of the connected compression web, the two tension webs, and the ceiling joist.

The center bracket allows the tension webs and compression web to be connected to the ceiling joist in a manner such that the tension webs and compression web do not have to overlie, or scab, the ceiling joist. This allows more of the steel frames to be stored or transported in a given area, because the tension webs, compression web, and the ceiling joist are within the same plane. Thus, the steel frame is only the thickness of one member instead of the thickness of two members. In addition, and also because the tension webs, compression web, and the ceiling joist are in the same plane, the load on the steel frame is more properly distributed throughout the steel frame, and the steel frame does not tend to torque under load. Further, the U shape of the center bracket allows it to receive tension webs, compression webs, and ceiling joists of any height, as the tension webs, compression webs, and ceiling joists can extend out the open end of the U shaped center brackets. In addition, the spine can be fastened to the ceiling joist through the holes in the spine, thereby greatly increasing the strength of the joint.

Channel brackets connect one of the tension webs and one of the compression webs to one of the rafters and the ceiling joist. The channel brackets have a length, width, and height, and also have a spine with two flaps adjacent the spine. The two flaps are disposed at ninety degree angles from the spine, such that the two flaps and the spine have a cross-section generally resembling a U shape. The spine has a predetermined number of holes in it, and each flap has at least twelve holes in it. The twelve holes in each flap are disposed such that four holes in each flap align with each of the connected compression web, tension web, and one of the rafter and ceiling joist.

The channel bracket allows the tension web and compression web to be connected to the one of the rafter and ceiling joist in a manner such that the tension web and compression web do not have to overlie, or scab, the one of the rafter and ceiling joist. This allows more of the steel frames to be stored or transported in a given area, because the tension web, compression web, and the one of the rafter and ceiling joist are within the same plane. Thus, the steel frame is only the thickness of one member instead of the thickness of two members. In addition, and also because the tension web, compression web, and the ceiling joist are in the same plane, the load on the steel frame is more properly distributed throughout the steel frame, and the steel frame does not tend to torque under load. Further, the U shape of the channel bracket allows it to receive tension webs, compression webs, and one of the rafter and ceiling joists of any height, as the tension webs, compression webs, and one of the rafter and ceiling joists can extend out the open end of the U shaped channel brackets. In addition, the spine can be fastened to the one of the rafter and ceiling joist through the holes in the spine, thereby greatly increasing the strength of the joint.

In an especially preferred embodiment, a wall portion of the frame is formed of studs, which are formed of the steel members. Truss brackets connect two of the studs to the ceiling joist. The truss brackets have a length, width, and height, and also have a spine with four flaps adjacent the spine. The four flaps are disposed at ninety degree angles from the spine, such that the four flaps and the spine have a cross-section generally resembling a U shape. The spine of the truss brackets is bendable to ninety degrees, such that when the spine is bent adjacent edges of adjacent flaps are also disposed at ninety degrees one to the other. The spine having a predetermined number of holes in it. Each flap also has at least four holes in it, where the four holes in each flap are disposed such that the four holes in each flap align with one of the ceiling joist and one of the connected studs, A floor joist having a height, and formed of the steel members, forms a floor portion of the steel frame. Stud brackets connect two of the studs to the floor joist. The stud brackets have a length, width, and height, and also have a spine with two flaps adjacent the spine. The two flaps are disposed at ninety degree angles from the spine, such that the two flaps and the spine have a cross-section generally resembling a U shape. The spine has a predetermined number of holes in it, and each flap has at least sixteen holes in it. The sixteen holes in each flap are disposed such that eight holes in each flap align with each of the connected stud and the floor joist.

Preferably, the alignment means of the peak bracket and eave brackets are scoring marks. Thus, when the spine is bent, an edge of an adjacent one of the four flaps is alignable to the scoring marks. Alternately, the alignment means are holes. Thus, when the spine is bent, the holes in one of the four flaps are alignable to the holes in an adjacent one of the four flaps. In various preferred embodiments, the predetermined number of holes in the spine of the peak bracket, channel bracket, center brackets, compression brackets, and stud brackets is one, two, or four per member adjacent the spine.

In an alternate embodiment of a construction system for building a steel frame using steel members, rafters, a ceiling joist, studs, compression webs, and tension webs are all formed of the steel members. The rafters form a roof portion of the steel frame, the ceiling joist, having two ends, forms a ceiling portion of the steel frame, and the studs form a wall portion of the steel frame. The compression webs are disposed between the rafters and the ceiling joists, and distribute load between the raters and the ceiling joists. The tension webs are disposed between the rafters, the ceiling joists, and the compression webs, and inhibit distortion of the roof.

Adjustable brackets are provided, having a length, width, and height, and a spine with four overlapping flaps adjacent the spine. The four flaps are disposed at ninety degree angles from the spine, such that the four flaps and the spine have a cross-section generally resembling a U shape. The spine is bendable to a variable degree at a position between the four flaps. At least one of the four flaps has scoring marks on it. When the spine is bent in a first direction, an edge of an adjacent one of the four flaps is alignable to the scoring marks. The scoring marks are calibrated in units that indicate the variable degree at which the spine is bent. The spine has a predetermined number of holes in it, and each flap has at least four holes in it.

A first of the adjustable brackets is bent in the first direction to a first desired variable degree. The first adjustable bracket connects two of the rafters together at a variable roof pitch, by connecting to three outside surfaces on each of the two rafters. Each of the two connected rafters thereby has a connected end and an unconnected end. The four holes in each flap of the first adjustable bracket are disposed such that the four holes in each flap align with one of the two connected rafters.

A second and a third of the adjustable brackets are bent in the first direction to a second desired variable degree. The second and third adjustable brackets connect the two unconnected ends of the two connected rafters to the ends of the ceiling joist, such that each end of the ceiling joist aligns with one of the unconnected ends of the two connected rafters. The four holes in each flap of the second and the third adjustable brackets are disposed such that the four holes in each flap align with one of the ceiling joist and the connected rafters.

A fourth and a fifth of the adjustable brackets are bent in a direction opposite the first direction to a ninety degree angle. The fourth and fifth adjustable brackets connect two of the studs to the ceiling joist. Channel brackets connect at least one of the tension webs and one of the compression webs to one of either the rafters or the ceiling joist. Each of the channel brackets has a length, width, and height, and also has a spine with two flaps adjacent the spine. The two flaps are disposed at ninety degree angles from the spine, such that the two flaps and the spine have a cross-section generally resembling a U shape. The spine has a predetermined number of holes in it, and each flap has at least twelve holes in it. The twelve holes in each flap are disposed such that four holes in each flap align with each of the connected compression web, tension web, and one of the rafter and ceiling joist.

In an embodiment of a construction system for connecting first and second members together at a variable angle, first and second slot brackets are provided, where each slot bracket has a spine with a predetermined number of holes in it. Two flaps are disposed adjacent the spine. One of each of the two flaps extends from opposite sides of the spine at about 90 degree angles, and each of the two flaps has at least six holes in it. A slot is disposed generally between the two flaps and at one end of the spine, such that the two flaps extend to a greater length than the spine. The two flaps and the spine of the first slot bracket receive the first member. The two flaps and the spine connect to three outside surfaces of the first member. The two flaps and the spine of the second slot bracket receive the second member. The two flaps and the spine connect to three outside surfaces of the second member. The two flaps of the first slot bracket overlap and connect to the two flaps of the second slot bracket.

BRIEF DESCRIPTION OF THE DRAWINGS

Further advantages of the invention will become apparent by reference to the detailed description when considered in conjunction with the figures, which are not to scale, wherein like reference numbers indicate like elements through the several views, and wherein:

FIGS. 6, 7A, and 7B are dimensional views of a peak bracket;

DETAILED DESCRIPTION

Figure 1:
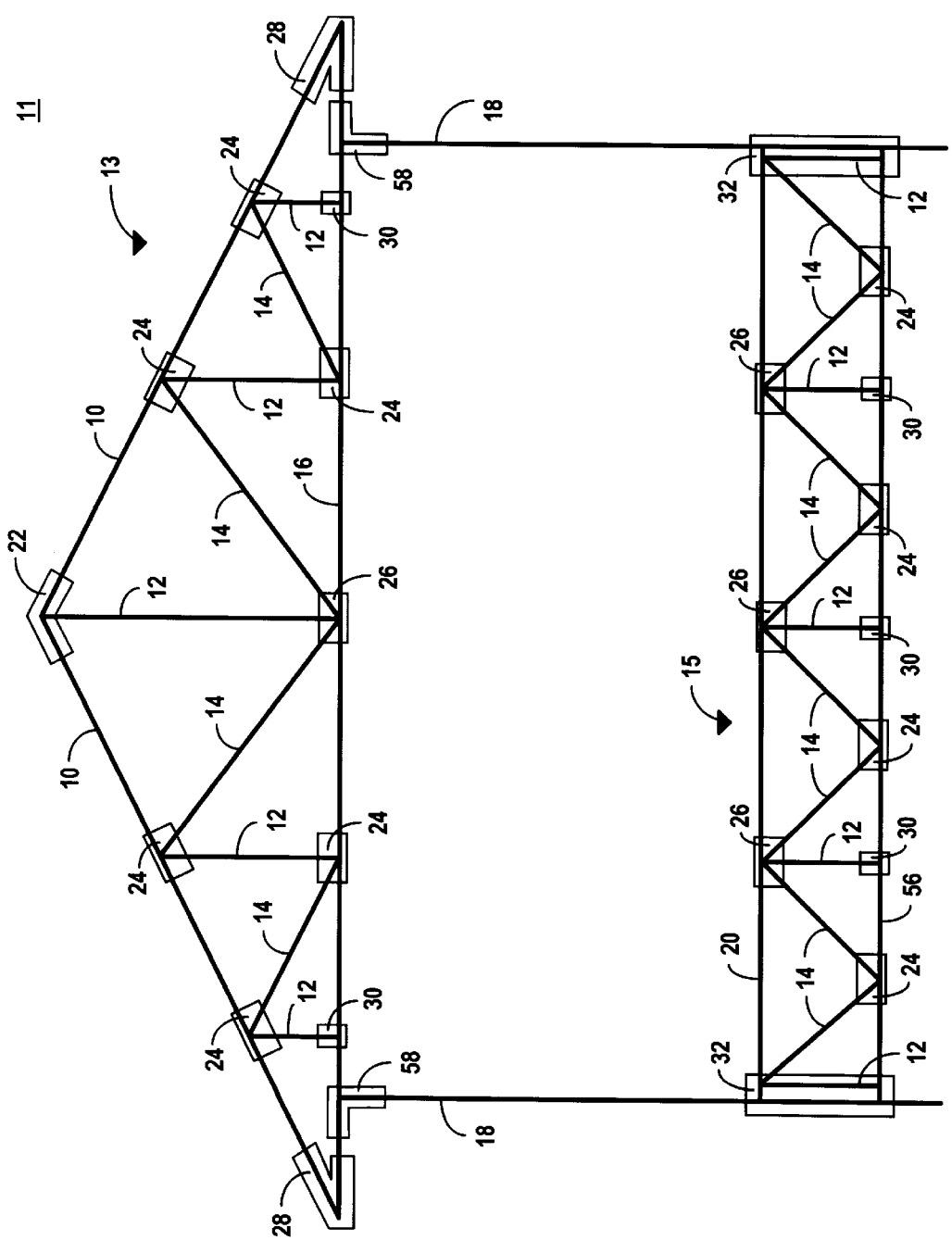
FIG. 1 depicts a steel building frame.

Referring now to FIG. 1, there is depicted a steel frame 11. The frame 11 comprises three major parts, being a truss 13, studs 18, and floor joist 15. The floor joist 15 is an optional part of the frame 11. The truss 13 is assembled from steel members, including rafters 10, ceiling joist 16, compression webs 12, and tension webs 14. While a specific arrangement of these members is depicted in FIG. 1, it will be appreciated that the invention as described herein is applicable to frames 11 of other engineering designs, and is not to be limited strictly to the representational design of FIG. 1.

In one embodiment, the truss 11 is assembled by cutting the rafters 10, ceiling joist 16, compression webs 12, and tension webs 14 to the proper length, and connecting them one to another using brackets. In various embodiments the brackets and members are pre-drilled or pierced with holes, and the brackets and members are connected using screws which are inserted through sets of aligned holes. In alternate embodiments, the brackets and members are not pre-drilled, and self-tapping screws are used to connect the brackets and members. In further embodiments, a combination of either the brackets or members or both are pre-drilled, and self-tapping steel screws are used, either in aligned sets of holes, or to create new connection points where needed.

The two rafters 10 and the main compression web 12, if used in the design, are connected together using a peak bracket 22, having a design and according to a method that will be described in more detail hereafter. Connecting one end each of the two rafters 10 leaves each rafter 10 with an unconnected end. The ceiling joist 16 is connected at the two unconnected ends of the rafters 10, using eave brackets 28. A center bracket 26 is used to connect the main compression web 12 and two tension webs 14, if used in the design, to the center of the ceiling joist 16. The unconnected ends of the two tension webs 14 connected to the ceiling joist 16 are connected to the two rafters 10 using channel brackets 24. Also connected to the rafters 10 with the channel brackets 24 are the tops of secondary compression webs 12, if used in the design. Channel brackets 24 are also used to connect the lower, unconnected ends of the secondary compression webs 12 to the ceiling joist 16. This method of supporting with compression webs 12 and tension webs 14 is continued as far as required by the design of the truss 13, as dictated by the requirements of the particular structure to be constructed. If the design requires that a compression web 12 be connected to the ceiling joist 16 without a tension web 14 connected at the same point, then the compression web 12 is connected to the ceiling joist 16 using a compression bracket 30.

The studs 18 are also formed of the steel members, and are connected at their tops, in the design depicted in FIG. 1, to the ceiling joist 16 using truss brackets 58. The floor joist 15 is connected at either end to the studs 18 using stud brackets 32. The floor joist 15 is constructed, according to the design depicted, with a floor joist top chord 20 and a floor joist bottom cord 56. Between the top chord 20 and the bottom cord 56 is a network of compression webs 12 and tension webs 14. These are connected to the top chord 20 and the bottom cord 56 using a combination of center brackets 26, channel brackets 24, and compression brackets 30. Generally speaking, a center bracket 26 is used wherever a combination of a single compression web 12 and two tension webs 14 are to be joined to either a top chord 20 or a bottom chord 56. A channel bracket 24 is used wherever either a combination of a single compression web 12 and a single tension web 14, or two tension webs 14, are to be joined to either a top chord 20 or a bottom chord 56. The compression brackets 30 are generally used wherever a single compression web 12 is to be joined to either a top chord 20 or a bottom chord 56. This same general selection criteria may be used for selecting brackets to connect the compression webs 12 and tension webs 14 to the rafters 10 and ceiling joist 16.

The frame 11 may be assembled in a piece-meal fashion, such as by bringing the members and brackets to an assembly point as each is required to be assembled, but more preferably is assembled by laying out all of the members of a component, such as either the truss 13 or the floor joist 15, and then with the members in their proper positions, connecting the members one to another using the appropriate brackets. The frame 11 can be assembled at the construction site, or can be assembled off-site and shipped to the construction site. If the frame 11 is to be shipped to the construction site, then the truss 13, studs 18, and floor joist 15 are preferably not assembled one to another, until they have been delivered to the construction site. In this manner, most of the assembly of the individual members and brackets can be completed off-site, yet the components are not so large as to present an insurmountable problem in shipping. Then, using just a few brackets to connect the studs 18 to the truss 13 and the floor joist 15, the final assembly of the frame 11 can be completed at the construction site.

All of the connected members used in the final assembly of the frame 11 are disposed within the same plane. In other words, none of the members are scabbed, or in other words, connected one to another by laying them on top of each other. This provides for several important benefits, including a stronger frame 11. The frame 11 is strong in this configuration because there are no torsional forces set up by load-bearing members applying force to other members in separate planes. Further, by having the frame 1 the thickness of a single member, instead of the frame 11 being the thickness of two or more members, as would be the case if they were connected by scabbing, more frames 11 may be shipped or stored within a given space. Thus, shipping and storage costs associated with the frames 11 may decrease.

Figure 23:
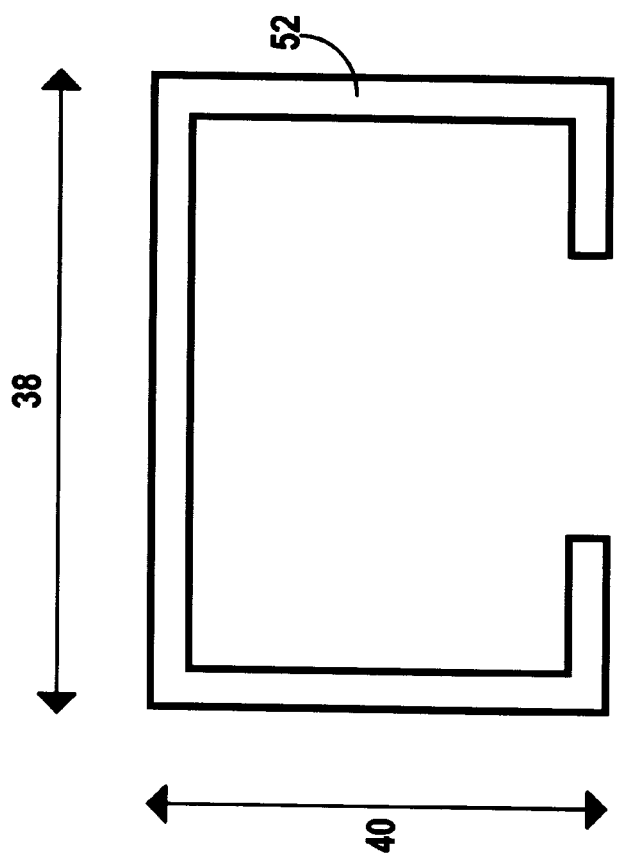
FIG. 23 is a cross-sectional view of C channel.

Because the members used to assemble the frame 11 are made of steel and not wood, they may be fashioned to any practical length required. Thus, the truss 13 and floor joist 15 may be fashioned to have a clear span that is much longer than is practical with a frame of wood construction. The steel members may be fashioned of any material having the proper load bearing capacity as required by the specific design of the building to be construction. Preferably the members are formed of twenty gauge steel, such as GVHD steel, with a cross-section as depicted in either FIG. 23 or FIG. 24. FIG. 23 depicts the cross-section of a C channel member 52, having a width 38 and a height 40. The length of the C channel can be as long as required, as described above. The C channel member 52 is partially open on one face. Thus, the C channel member 52 may be formed from a roll of steel plate that is formed into the C channel configuration by a continuous process. Either prior to or during this forming process the steel plate can be pierced with holes as desired.

Figure 24:
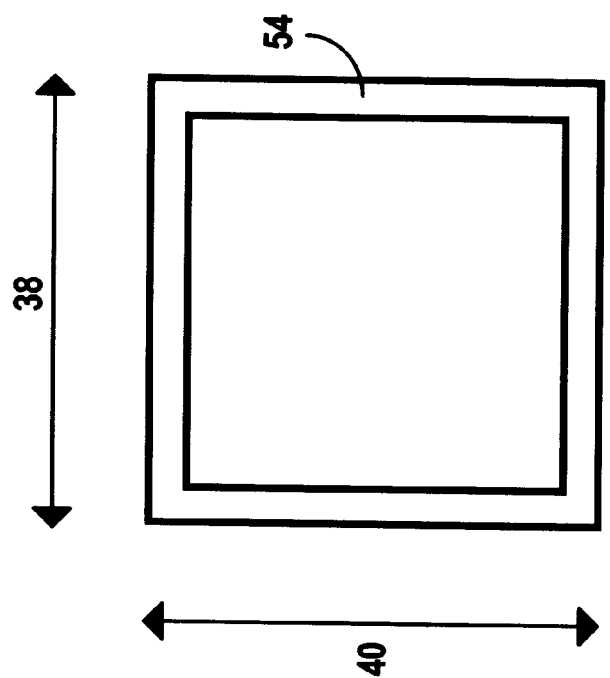
FIG. 24 is a cross-sectional view of box channel.

FIG. 24 depicts the cross-section of a box channel member 54, also having a width 38 and a height 40. Of course, as mentioned above, the box channel member 54 may also be as long as desired, within the load bearing constraints of the material selected for its construction and the design of the building. Preferably, the width of either the C channel members 52 or box channel members 54 is about two inches. In an alternate embodiment the width is about 1.75 inches. However, it will be appreciated that this width may also be modified according to the material selected and the design of the building. The width selected will have an impact on the design of the brackets, as described in more detail below. The height 40 of the members is preferably between about three inches and about six inches. However, this dimension also can be adjusted in alternate embodiments, within the constraints previously mentioned above for the width of the members.

The frame 11 may be constructed entirely of either C channel 52 or box channel 54. However, in one preferred embodiment, the frame 11 is constructed of a combination of C channel 52 and box channel 54, which provides powerful benefits, as described more completely below.

Figure 2:
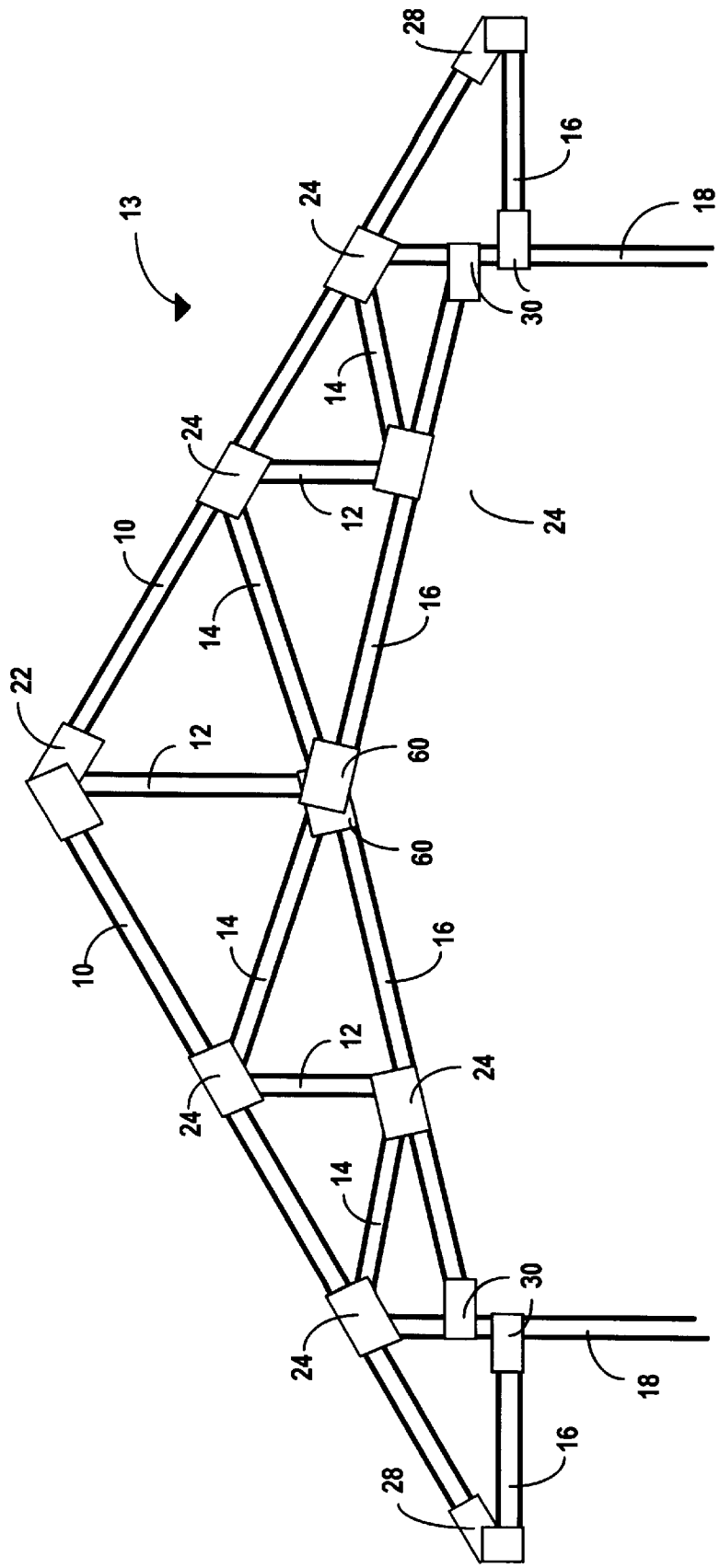
FIG. 2 depicts a cathedral truss.

In FIG. 2 there is depicted an alternate embodiment of the truss 13. In this embodiment, the bottom chord of the truss 13 is formed of two ceiling joists 16, instead of from a single ceiling joist 16, as depicted in FIG. 1. This configuration requires an additional bracket to connect the interior ends of the ceiling joists 16 together, and to any compression webs 12 and tension webs 14 that may be connected to the ceiling joists 16 at the same position. Thus, instead of a center bracket 26, two slot brackets 60 are used to connect these members one to another. The unique design of the slot bracket 60, as described more completely below, allows members to be connected at an interior angle, rather than an exterior angle such as is created at the peak of the rafters 10 with the peak bracket 22.

Figure 3:
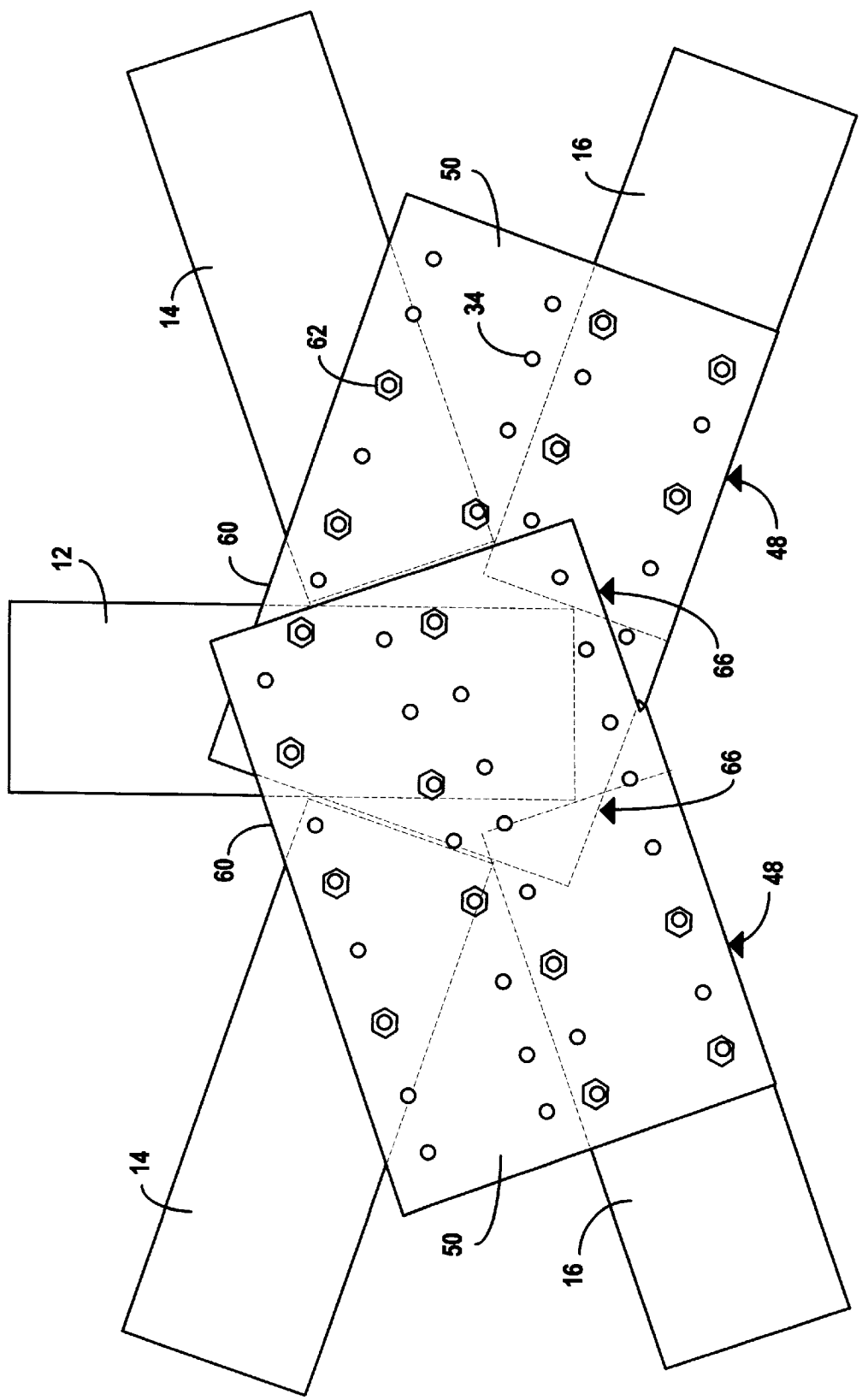
FIG. 3 is a detail view of slot brackets.
Figure 4:
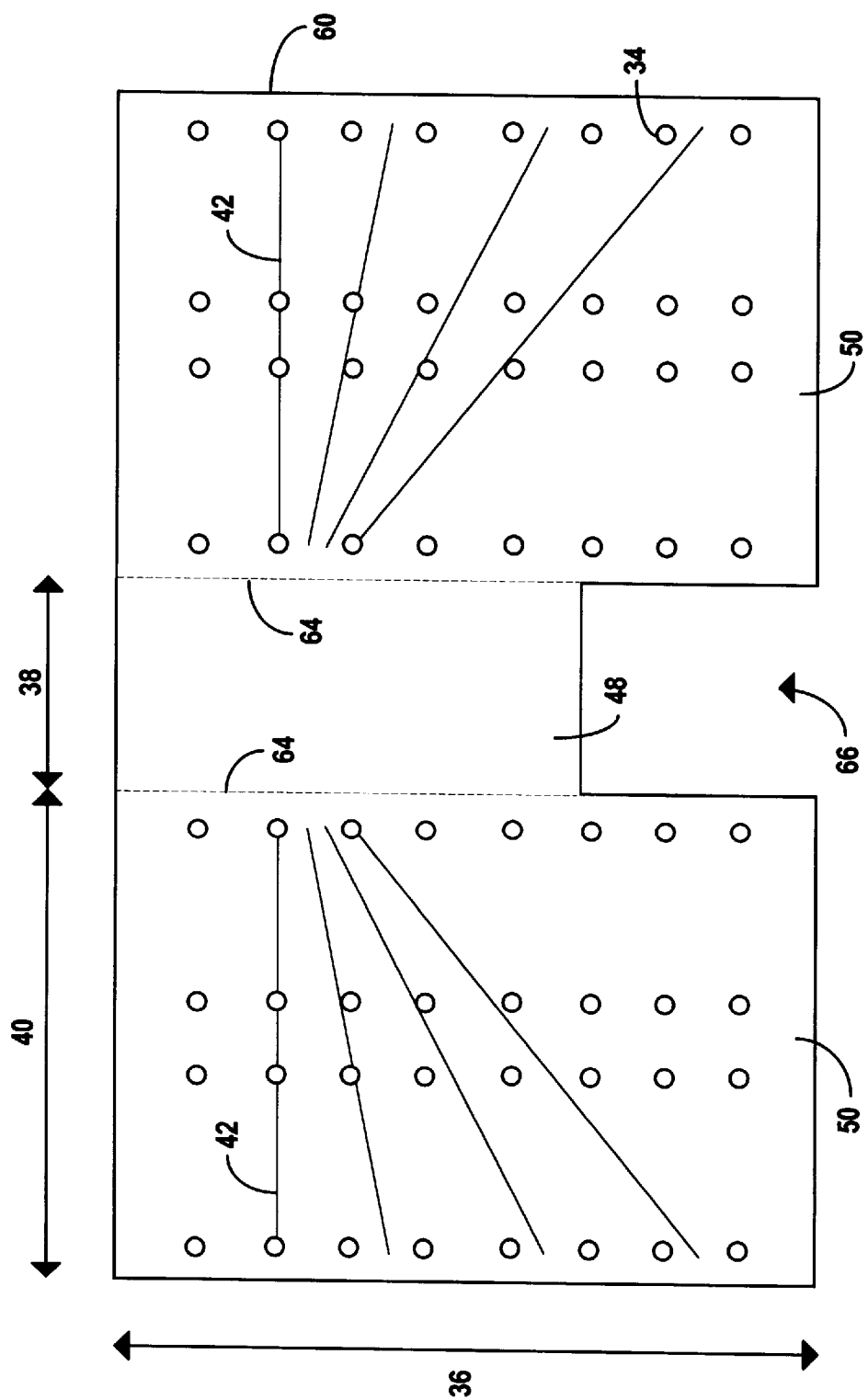
FIG. 4 is a dimensional view of a slot bracket.

FIG. 3 depicts the detail of two slot brackets 60 used to connect two ceiling joists 16 to two tensions webs 14 and a compression web 12. Reference is also made to FIG. 4, which is a dimensional depiction of the slot bracket 60. The slot bracket 60 and its method of use will be most clearly understood during the following description by reference to both FIGS. 3 and 4. The slot bracket 60 has a spine 48 disposed between two flaps 50. The two flaps 50 are bent upwards in the same direction from the spine 48 along bend lines 64, to about ninety degrees. Thus, the slot bracket 60 has a generally U shaped cross-section. The slot bracket 60 has a width 38, which is also the width of the spine 48, and which is designed to be substantially the same as the width 38 of the members which the slot bracket 60 is intended to connect together. The slot bracket 60 has a length 36, which is also the length of the flaps 50. However, the length of the spine 48 is shorter than the length 36 of the slot bracket 60, thus forming slot 66. As discussed above, in one embodiment the slot bracket 60 is pre-drilled with holes 34.

One end of a ceiling joist 16 is inserted into a slot bracket 60, as depicted in FIG. 3. The ceiling joist 16 is inserted such that the spine 48 of the slot bracket 60 is disposed adjacent the width 38 of the ceiling joist 16. Thus, the two flaps 50 of the slot bracket 60 are disposed adjacent opposing sides of the ceiling joist 16, with the slot 66 extending past the interior end of the ceiling joist 16. Steel fasteners, such as screws 62, are used to connect the slot bracket 60 to the ceiling joist 16. As discussed above, the screws 62 may be placed in the pre-drilled holes 34, or self-tapping screws 62 may be used and placed where desired, or a combination of both methods may be used.

Four screws 62 are preferably used to fasten each flap of the slot bracket 60 to the opposing sides of the ceiling joist 16, and one, two, or four screws 62 are preferably used to fasten the spine 48 of the slot bracket 60 to the face of the ceiling joist 16. Thus, regardless of the connection method used, as described above, there are at least four holes in each flap that align with at least four holes in each side of the ceiling joist 16. In this manner, the slot bracket 60 is fastened on three sides to the ceiling joist 16, thus providing a very strong connection to the ceiling joist 16.

A second slot bracket 60 is connected to the interior end of a second ceiling joist 16, in a manner similar to that as described above. Those portions of the slots 66 and the flaps 50 of the two slot brackets 60 which extend beyond the interior ends of the ceiling joists 16 are engaged, such that the flaps 50 of the different slot brackets 60 overlap one another, and the spines 48 of the different slot brackets 60 either meet or very nearly meet. The other members to be connected within the slot bracket 60, such as the compression web 12 and two tensions webs 14 as depicted in FIG. 3, are brought within the trough formed by the overlapping flaps 50, and connected to the flaps 50 of the slot brackets 60 on two opposing sides of each member with screws 62.

The slot brackets 60 preferably have alignment means, such as score marks 42 disposed on the outer face of at least one of the flaps 50. The end of a flap 50 on one of the slot brackets 60 is aligned with the score mark 42 on the overlapped flap 50 of the other slot bracket 60. The score marks 42 are calibrated with indicia, not depicted, which indicate the angle at which the score marks 42 are disposed relative to the spine 48 of the slot bracket 60. In this manner, the proper angle, as required by the design for the truss 13, can be readily and accurately set between the ceiling joists 16, without the need for additional or elaborate jigs, gauges, or equipment. This can be of tremendous benefit, especially when assembling trusses 13 at the construction site.

The height 40 of the slot brackets 60 is preferably about twice the height 40 of the steel members used. Thus, if steel members having a height 40 of about three inches are used, then the height 40 of the slot bracket 60 is preferably about six inches. Similarly, if steel members having a height 40 of about six inches are used, then the height 40 of the slot bracket 60 is preferably about twelve inches. In the preferred embodiment, all of the various members used have the same height 40 and width 38. However, in alternate embodiments, the members are of different heights 40 or widths 38, and the brackets are adjusted accordingly.

The length 36 of the slot brackets 60 is preferably about three times the height 40 of the members used. The length of the spine 48 of the slot bracket is equal to approximately two-thirds of this length 36, which means that the slot 66 has a length that is approximately equal to the height 40 of the members used. The interior ends of the ceiling joists 16 can be inserted into the slot brackets 60 to the full length of the spine 48, or just far enough into the slot bracket 60 to provide an adequate length to connect the slot bracket 60 to the ceiling joist 16, while still leaving sufficient space to insert and connect another member, such as the compression web 12, between the two ceiling joists 16.

A peak bracket 22 is depicted in FIGS. 5, 6, and 7A–7B. The peak bracket 22 and its method of use will be most clearly understood during the following description by reference to all of FIGS. 5–7B. Peak bracket 22 has a spine 48, which is flanked on either side by four flaps 50. The flaps 50 are all folded up in the same direction at bend lines 64, so that the peak bracket 22 has a generally U shaped cross-section. The peak bracket 22 has a width 38, which is also the width of the spine 48, and which is designed to be substantially the same as the width 38 of the members which the peak bracket 22 is intended to connect together. The peak bracket 22 has a length 36, which is also the length of two of the flaps 50. As discussed above, in one embodiment the peak bracket 22 is pre-drilled with holes 34.

Figure 5:
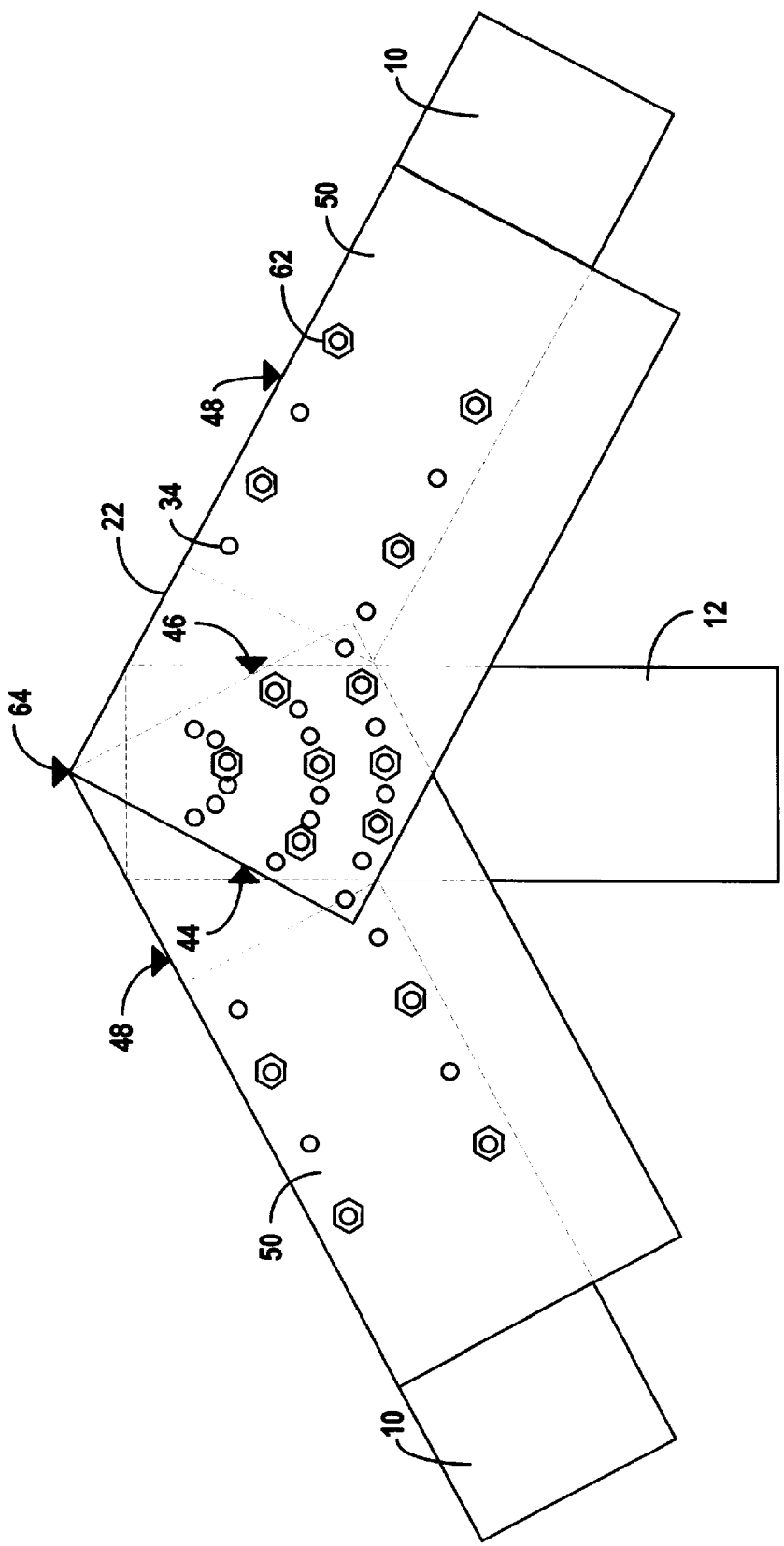
FIG. 5 is a detail view of a peak bracket.

One end of a rafter 10 is inserted into a peak bracket 22, as depicted in FIG. 5. The rafter 10 is inserted such that the spine 48 of the peak bracket 22 is disposed adjacent the width 38 of the rafter 10. Thus, two of the flaps 50 of the peak bracket 22 are disposed adjacent opposing sides of the rafter 10, with the other two flaps 50, and that portion of the spine 48 which is disposed between them, extending past the interior end of the rafter 10. Steel fasteners, such as screws 62, are used to connect the peak bracket 22 to the rafter 10. As discussed above, the screws 62 may be placed in the pre-drilled holes 34, or self-tapping screws 62 may be used and placed where desired, or a combination of both methods may be used.

Four screws 62 are preferably used to fasten each flap of the peak bracket 22 to the opposing sides of the rafter 10, and one, two, or four screws 62 are preferably used to fasten the spine 48 of the peak bracket 22 to the face of the rafter 10. Thus, regardless of the connection method used, as described above, there are at least four holes in each of the two connected flaps 50 that align with at least four holes in each side of the rafter 10. In this manner, the peak bracket 22 is fastened on three side to the rafter 10, thus providing a very strong connection to the rafter 10.

The other end of the peak bracket 22 is connected to the interior end of a second rafter 10, in a manner similar to that as described above. The peak bracket 22 is bendable to a degree at a bend line 64 disposed transverse the spine 48 at a position between the sets of two flaps 50 at either end of the peak bracket 22. The peak bracket 22 is preferably bent to a first exterior angle, such that the flaps 50 of the different ends of the peak bracket 22 overlap one another. The other members to be connected within the peak bracket 22, such as the compression web 12 as depicted in FIG. 5, are brought within the trough formed by the overlapping flaps 50, and connected to the flaps 50 of the peak bracket 22 on two opposing sides of the member with screws 62.

The peak bracket 22 preferably has alignment means, such as score marks 42 as depicted in FIG. 7A, disposed on the outer face of at least one of the flaps 50. The edge 44 of a flap 50 on one end of the peak bracket 22 is aligned with the score mark 42 on the overlapped flap 50 on the other end of the peak bracket 22. The score marks 42 are calibrated with indicia, not depicted, which indicate the angle at which the score marks 42 are disposed relative to the spine 48 of the peak bracket 22. In this manner, the proper angle, as required by the design for the truss 13, can be readily and accurately set between the rafters 10, without the need for additional or elaborate jigs, gauges, or equipment. This can be of tremendous benefit, especially when assembling trusses 13 at the construction site.

Figure 6:
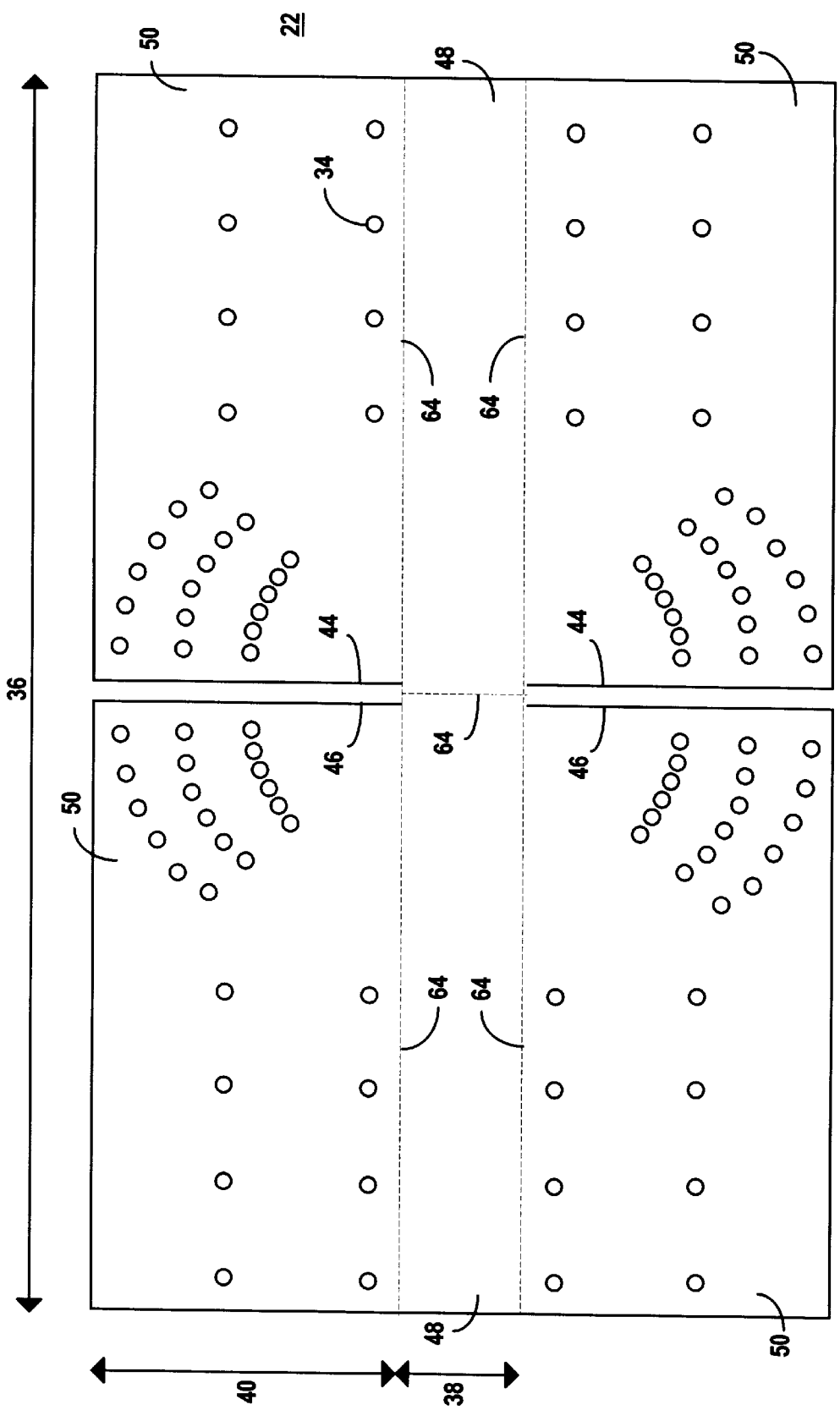

Alternately, the peak bracket 22 has alignment means, such as holes 34 disposed in arc-shaped patterns as depicted in FIGS. 5 and 6, disposed on the face of adjacent ones of the flaps 50. The holes 34 in a flap 50 on one end of the peak bracket 22 are aligned with the holes 34 on the overlapped flap 50 on the other end of the peak bracket 22. The holes 34 are calibrated with indicia, not depicted, which indicate the angle at which the holes 34 are disposed relative to the spine 48 of the peak bracket 22. In this manner, the proper angle, as required by the design for the truss 13, can be readily and accurately set between the rafters 10, without the need for additional or elaborate jigs, gauges, or equipment. This can be of tremendous benefit, especially when assembling trusses 13 at the construction site.

The height 40 of the peak bracket 22 is preferably about fifty percent greater than the height 40 of the steel members used. Thus, if steel members having a height 40 of about three inches are used, then the height 40 of the peak bracket 22 is preferably about four and a half inches. Similarly, if steel members having a height 40 of about six inches are used, then the height 40 of the peak bracket 22 is preferably about nine inches. In the preferred embodiment, all of the various members used have the same height 40 and width 38. However, in alternate embodiments, the members are of different heights 40 or widths 38, and the brackets are adjusted accordingly.

The length 36 of the peak bracket 22 is preferably about six times the height 40 of the members used. The length of the spine 48 one end of the slot bracket is equal to approximately one-half of this length 36, which means that the flaps 50 on either side of the bend line 64 in the middle of the spine 48 have a length that is approximately equal to three times the height 40 of the members used. The interior ends of the rafters 10 can be inserted into the peak bracket 22 to the full length of the flaps 50, or just far enough into the peak bracket 22 to provide an adequate length to connect the peak bracket 22 to the rafter 10, while still leaving sufficient space to insert and connect another member, such as the compression web 12, between the two rafters 10.

Figure 8:
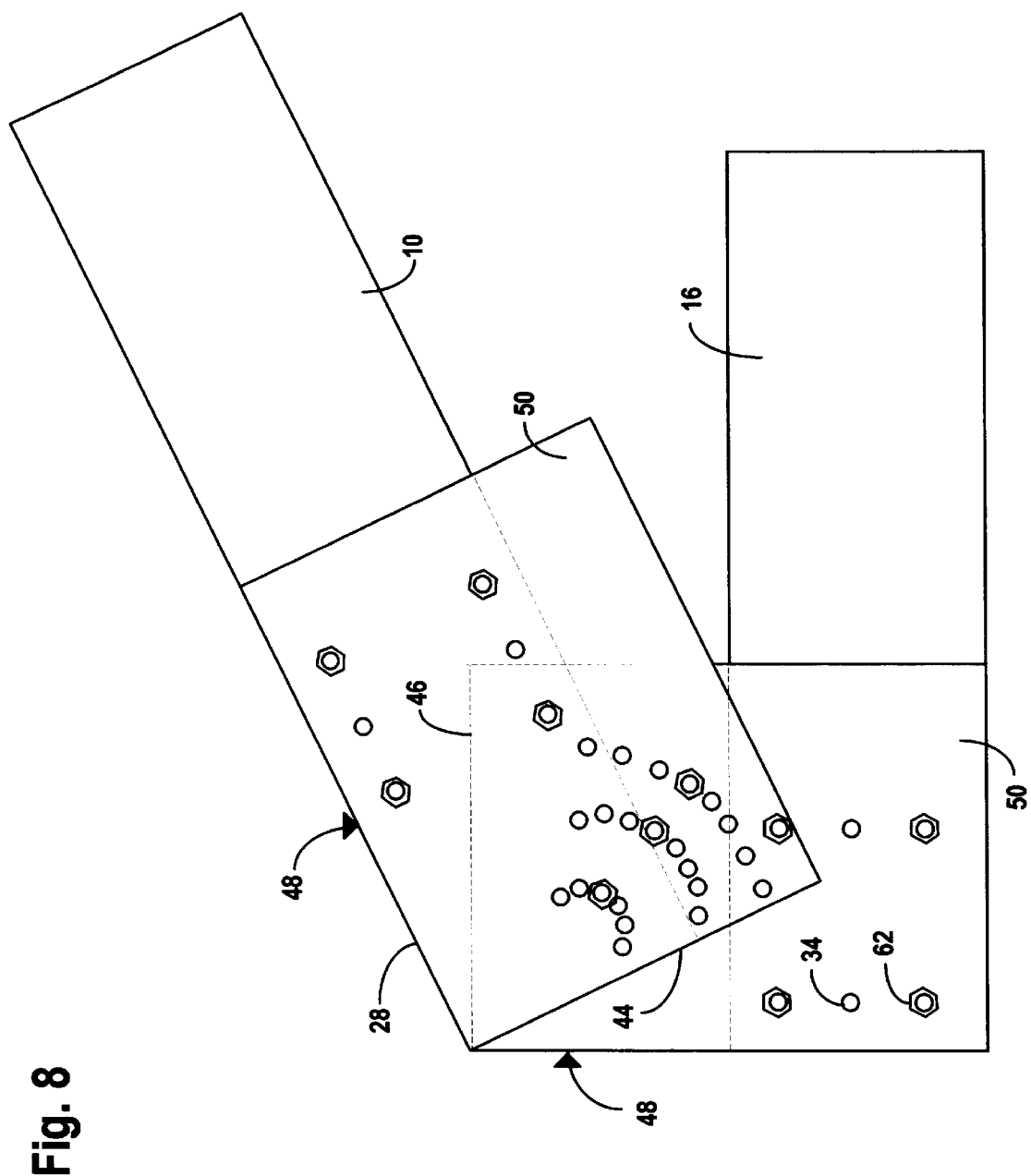
FIG. 8 is a detail view of an eave bracket.
Figure 9:
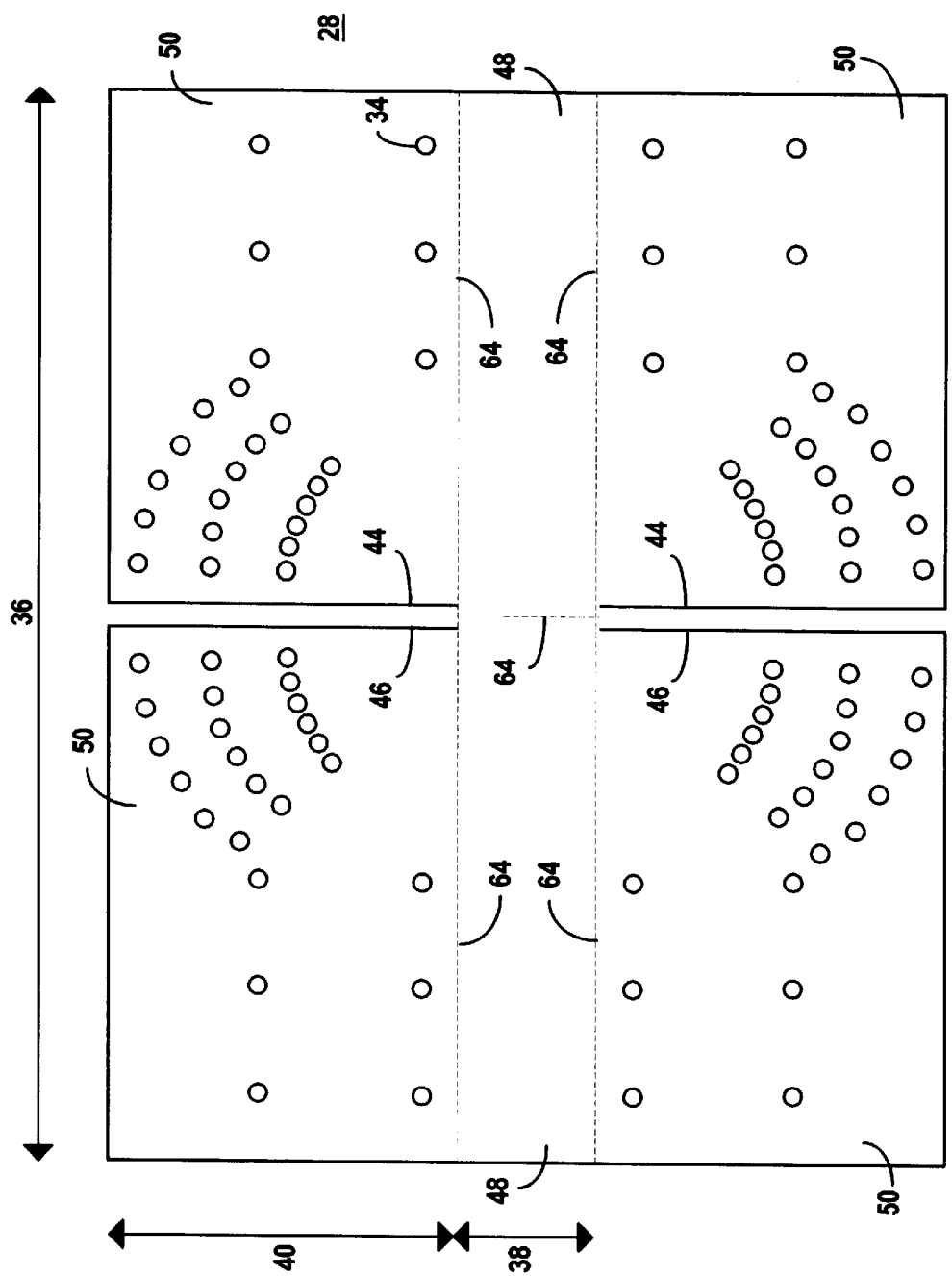
FIG. 9 is a dimensional view of an eave bracket.

FIG. 8 depicts the detail of an eave bracket 28, used to connect the exterior or unconnected end of a rafter 10 to one of the ends of the ceiling joist 16. Reference is also made to FIG. 9, which is a dimensional depiction of the eave bracket 28. The eave bracket 28 and its method of use will be most clearly understood during the following description by reference to both FIGS. 8 and 9. Eave bracket 28 has a spine 48, which is flanked on either side by four flaps 50. The flaps 50 are all folded up in the same direction at bend lines 64, so that the eave bracket 28 has a generally U shaped cross-section. The eave bracket 28 has a width 38, which is also the width of the spine 48, and which is designed to be substantially the same as the width 38 of the members which the eave bracket 28 is intended to connect together. The eave bracket 28 has a length 36, which is also the length of two of the flaps 50. As discussed above, in one embodiment the eave bracket 28 is pre-drilled with holes 34.

The exterior end of the rafter 10 is inserted into an eave bracket 28, as depicted in FIG. 8. The rafter 10 is inserted such that the spine 48 of the eave bracket 28 is disposed adjacent the width 38 of the rafter 10. Thus, two of the flaps 50 of the eave bracket 28 are disposed adjacent opposing sides of the rafter 10, with the other two flaps 50, and that portion of the spine 48 which is disposed between them, extending past the exterior end of the rafter 10. Steel fasteners, such as screws 62, are used to connect the eave bracket 28 to the rafter 10. As discussed above, the screws 62 may be placed in the pre-drilled holes 34, or self-tapping screws 62 may be used and placed where desired, or a combination of both methods may be used.

Four screws 62 are preferably used to fasten each flap of the eave bracket 28 to the opposing sides of the rafter 10, and one, two, or four screws 62 are preferably used to fasten the spine 48 of the eave bracket 28 to the face of the rafter 10. Thus, regardless of the connection method used, as described above, there are at least four holes in each of the two connected flaps 50 that align with at least four holes in each side of the rafter 10. In this manner, the eave bracket 28 is fastened on three side to the rafter 10, thus providing a very strong connection to the rafter 10.

The other end of the eave bracket 28 is connected to one end of the ceiling joist 16, in a manner somewhat different from that as described above. The spine 48 of the eave bracket 28 is disposed adjacent the end of the cut length of the ceiling joist 16. Thus, there is no face of the ceiling joist 16 disposed adjacent the spine 48 of the eave bracket 28, and the spine 48 cannot be connected to the ceiling joist 16. However, the two flaps 50 of the eave bracket 28, disposed at that end of the eave bracket 28, can be connected to the opposing outside surfaces of the ceiling joist 16, using screws 62. Thus, four holes 34 in each of the two flaps 50 are aligned with holes 34 in the ceiling joist 16, and the ceiling joist 16 is securely connected to the eave bracket 28.

The eave bracket 28 is bendable to a degree at a bend line 64 disposed transverse the spine 48 at a position between the sets of two flaps 50 at either end of the eave bracket 28. The eave bracket 28 is preferably bent to a second exterior angle, such that the flaps 50 at the different ends of the eave bracket 28 overlap one another. The eave bracket 28 preferably has alignment means, such as score marks 42, similar to those of the peak bracket 22 as depicted in FIG. 7A, disposed on the outer face of at least one of the flaps 50. The end of a flap 46 on one end of the eave bracket 28 is aligned with the score mark 42 on the overlapped flap 50 on the other end of the eave bracket 28. The score marks 42 are calibrated with indicia, not depicted, which indicate the angle at which the score marks 42 are disposed relative to the spine 48 of the eave bracket 28. In this manner, the proper angle, as required by the design for the truss 13, can be readily and accurately set between the rafters 10, without the need for additional or elaborate jigs, gauges, or equipment. This can be of tremendous benefit, especially when assembling trusses 13 at the construction site.

Alternately, the eave bracket 28 has alignment means, such as holes 34 disposed in arc-shaped patterns as depicted in FIGS. 8 and 9, disposed on the face of adjacent ones of the flaps 50. The holes 34 in a flap 50 on one end of the eave bracket 28 are aligned with the holes 34 on the overlapped flap 50 on the other end of the eave bracket 28. The holes 34 are calibrated with indicia, not depicted, which indicate the angle at which the holes 34 are disposed relative to the spine 48 of the eave bracket 28. In this manner, the proper angle, as required by the design for the truss 13, can be readily and accurately set between the rafter 10 and ceiling joist 16, without the need for additional or elaborate jigs, gauges, or equipment. This can be of tremendous benefit, especially when assembling trusses 13 at the construction site.

The height 40 of the eave bracket 28 is preferably about fifty percent greater than the height 40 of the steel members used. Thus, if steel members having a height 40 of about three inches are used, then the height 40 of the eave bracket 28 is preferably about four and a half inches. Similarly, if steel members having a height 40 of about six inches are used, then the height 40 of the eave bracket 28 is preferably about nine inches. In the preferred embodiment, all of the various members used have the same height 40 and width 38. However, in alternate embodiments, the members are of different heights 40 or widths 38, and the brackets are adjusted accordingly.

The length 36 of the eave bracket 28 is preferably about four times the height 40 of the members used. The length of the spine 48 one end of the slot bracket is equal to approximately one-half of this length 36, which means that the flaps 50 on either side of the bend line 64 in the middle of the spine 48 have a length that is approximately equal to twice the height 40 of the members used. The exterior end of the rafter 10 can be inserted into the eave bracket 28 to the full length of the flaps 50, or just far enough into the eave bracket 28 to provide an adequate length to connect the eave bracket 28 to the rafter 10. Similarly, the end of the ceiling joist 16 can be inserted into the eave bracket 28 to the full width 40 of the flaps 50, or just far enough into the eave bracket 28 to provide an adequate width to connect the eave bracket 28 to the ceiling joist 16.

As can be seen by comparing the peak bracket 22, depicted in FIGS. 5–7B, to the eave bracket 28, depicted in FIGS. 8 and 9, the peak bracket 22 and the eave bracket 28 are extremely similar. In one embodiment, the peak bracket 22 and the eave bracket 28 are used interchangeably. Because the peak bracket 22 and the eave bracket 28 are bendable at the bend line 64 on the spine 48 to variable degrees, a single peak bracket 22 or eave bracket 28 may be used to build trusses 13 having a wide variety of roof pitches. In other words, a different peak bracket 22 and eave bracket 28 are not required for one roof with a steep pitch and another roof with a shallow pitch. The alignment means used to set the angle between the members which the peak bracket 22 and the eave bracket 28 connect may be marked either in degrees or in roof pitch, to simplify the bending of the spine 48 and the alignment of the respective members.

Figure 10:
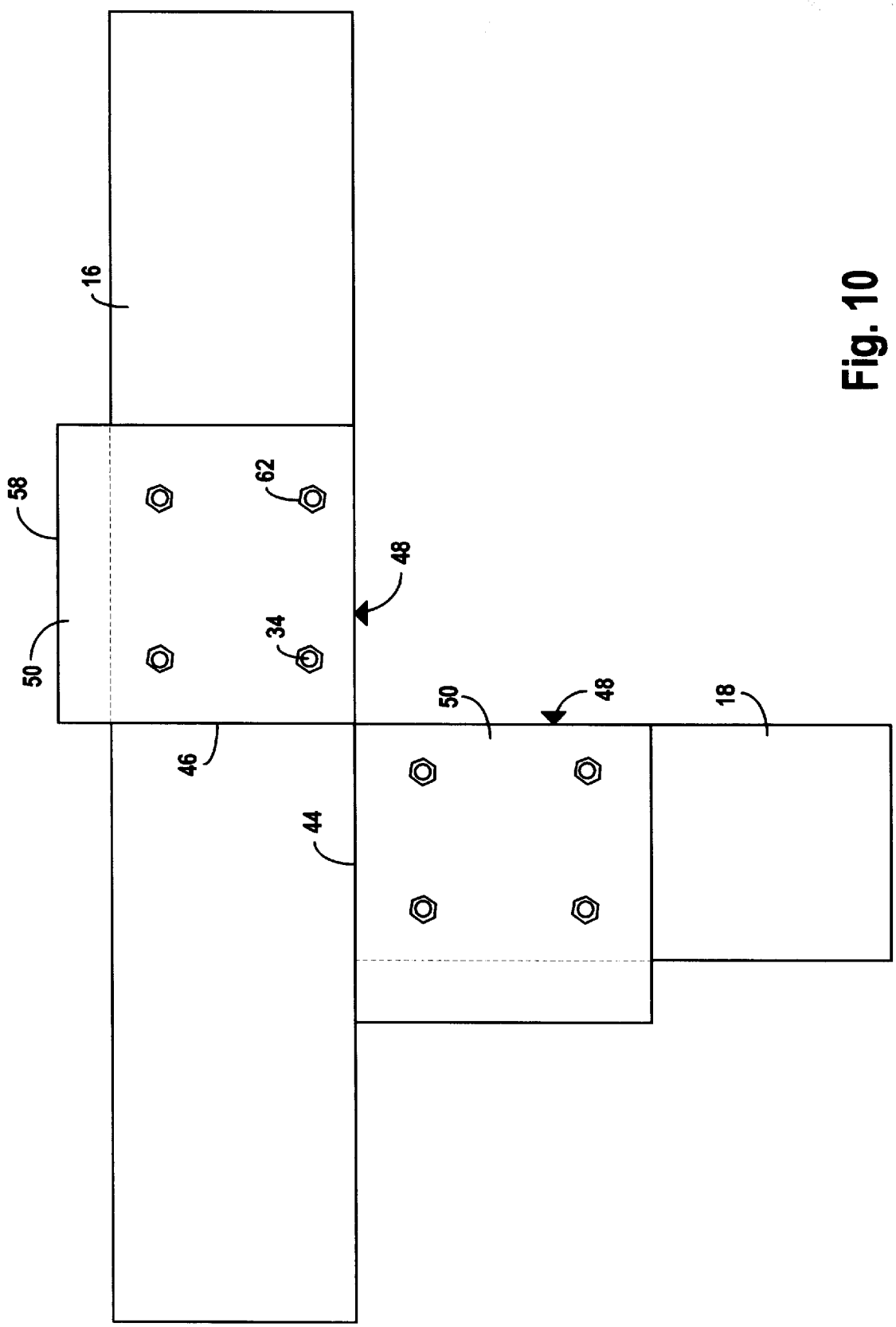
FIG. 10 is a detail view of a truss bracket.
Figure 11:
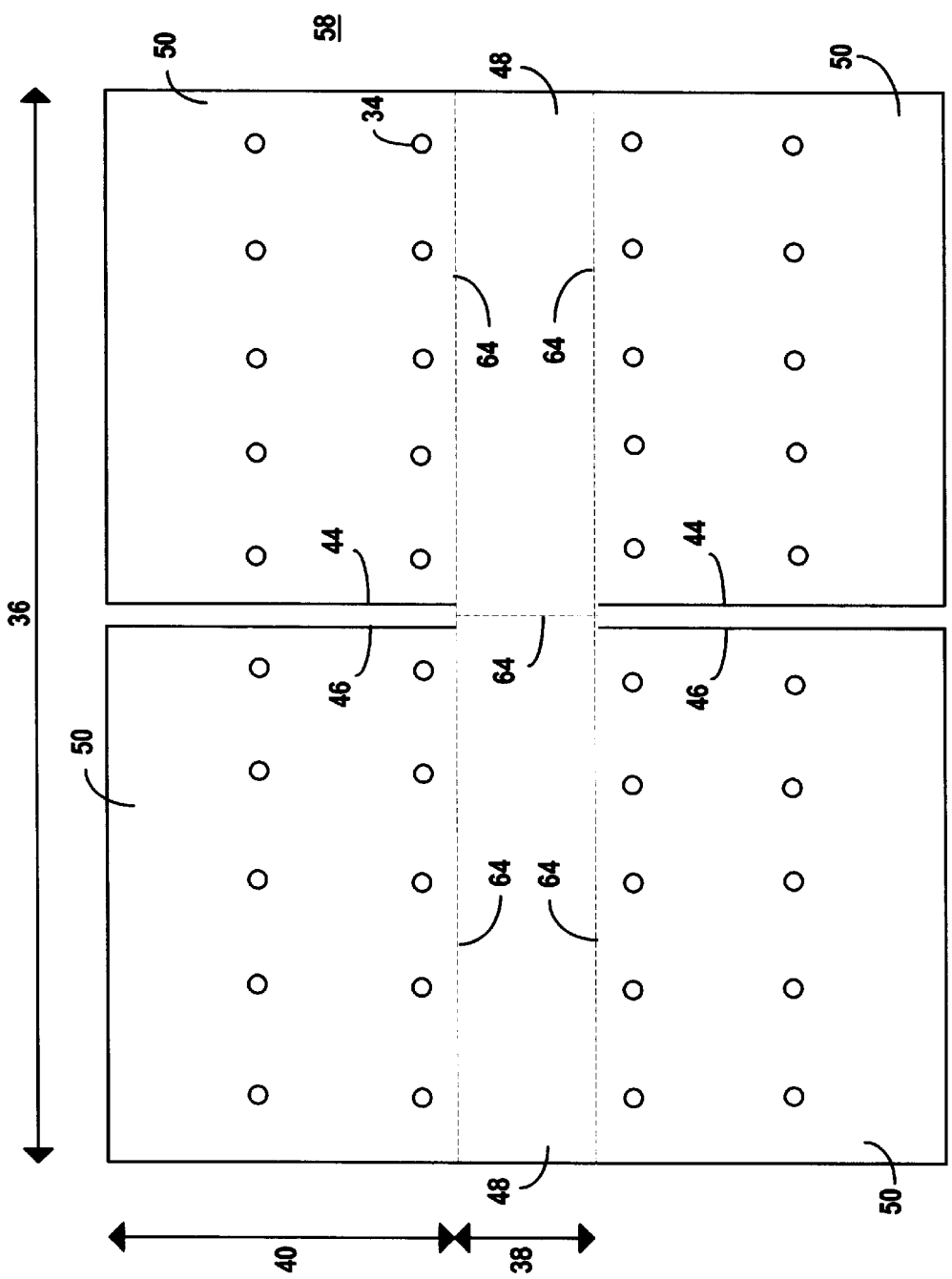
FIG. 11 is a dimensional view of a truss bracket.

FIG. 10 depicts the detail of a truss bracket 58, used to connect the top end of a stud 18 to a point near one of the ends of the ceiling joist 16. Reference is also made to FIG. 11, which is a dimensional depiction of the truss bracket 58. The truss bracket 58 and its method of use will be most clearly understood during the following description by reference to both FIGS. 10 and 11. Truss bracket 58 has a spine 48, which is flanked on either side by four flaps 50. The flaps 50 are all folded up in the same direction at bend lines 64, so that the truss bracket 58 has a generally U shaped cross-section. The truss bracket 58 has a width 38, which is also the width of the spine 48, and which is designed to be substantially the same as the width 38 of the members which the truss bracket 58 is intended to connect together. The truss bracket 58 has a length 36, which is also the length of two of the flaps 50. As discussed above, in one embodiment the truss bracket 58 is pre-drilled with holes 34.

The top end of the stud 18 is inserted into a truss bracket 58, as depicted in FIG. 10. The stud 18 is inserted such that the spine 48 of the truss bracket 58 is disposed adjacent the width 38 of the stud 18. Thus, two of the flaps 50 of the truss bracket 58 are disposed adjacent opposing sides of the stud 18, with the other two flaps 50, and that portion of the spine 48 which is disposed between them, extending past the top end of the stud 18. Steel fasteners, such as screws 62, are used to connect the truss bracket 58 to the stud 18. As discussed above, the screws 62 may be placed in the pre-drilled holes 34, or self-tapping screws 62 may be used and placed where desired, or a combination of both methods may be used.

Four screws 62 are preferably used to fasten each flap of the truss bracket 58 to the opposing sides of the stud 18, and one, two, or four screws 62 are preferably used to fasten the spine 48 of the truss bracket 58 to the face of the stud 18. Thus, regardless of the connection method used, as described above, there are at least four holes in each of the two connected flaps 50 that align with at least four holes in each side of the stud 18. In this manner, the truss bracket 58 is fastened on three side to the stud 18, thus providing a very strong connection to the stud 18.

The other end of the truss bracket 58 is connected to a position near one end of the ceiling joist 16, in a manner somewhat similar to that as described above, except that the end of the ceiling joist 16 is not inserted into the truss bracket 58. Rather, the truss bracket 58 connects to a point between the two ends of the ceiling joist 16, preferably near one end of the ceiling joist 16. In order for this to be accomplished, the truss bracket 58 needs to be bent in a manner different from that as described above for the peak bracket 22 and the eave bracket 28.

The truss bracket 58 is bendable to a degree at a bend line 64 disposed transverse the spine 48 at a position between the sets of two flaps 50 at either end of the truss bracket 58. The truss bracket 58 is preferably bent to an interior angle in a second direction, opposite those angles to which the peak bracket 22 and the eave brackets 28 are bent, such that the adjacent edges 46 and 44 of adjacent flaps 50 at the different ends of the truss bracket 58 form a ninety degree angle when the spine 48 is bent to a ninety degree interior angle.

The height 40 of the truss bracket 58 is preferably about fifty percent greater than the height 40 of the steel members used. Thus, if steel members having a height 40 of about three inches are used, then the height 40 of the truss bracket 58 is preferably about four and a half inches. Similarly, if steel members having a height 40 of about six inches are used, then the height 40 of the truss bracket 58 is preferably about nine inches. In the preferred embodiment, the studs 18 have a greater height 40 than the other members. However, in alternate embodiments, the members have the same height 40 and width 38, and the brackets are adjusted accordingly.

The length 36 of the truss bracket 58 is preferably about four times the height 40 of the members used. The length of the spine 48 one end of the slot bracket is equal to approximately one-half of this length 36, which means that the flaps 50 on either side of the bend line 64 in the middle of the spine 48 have a length that is approximately equal to twice the height 40 of the members used. The top end of the stud 18 is preferably inserted into the truss bracket 58 to the full length of the flaps 50. As mentioned above, the ceiling joist 16 is connected at a position between the two ends of the ceiling joist 16.

As can be seen by comparing the truss bracket 58 to the peak bracket 22 and the eave bracket 28, the peak bracket 22, eave bracket 28, and truss bracket 58 are extremely similar. In one embodiment, the peak bracket 22, eave bracket 58, and truss bracket 58 are used interchangeably. While the truss bracket 58 does not require alignment means, such as score marks 42, or holes 34 disposed in arc-shaped patterns, as do the peak bracket 22 and eave bracket 28, such alignment means do not inhibit the operation or utility of the truss bracket 58. Thus, a single adjustable bracket, with alignment means, may be used as the peak bracket 22, eave bracket 28, and truss bracket 58.

In an alternate embodiment, the studs 18 are connected to the ceiling joist 16 by means of a compression bracket 30, in a manner that is described with more particularity below.

Figure 12:
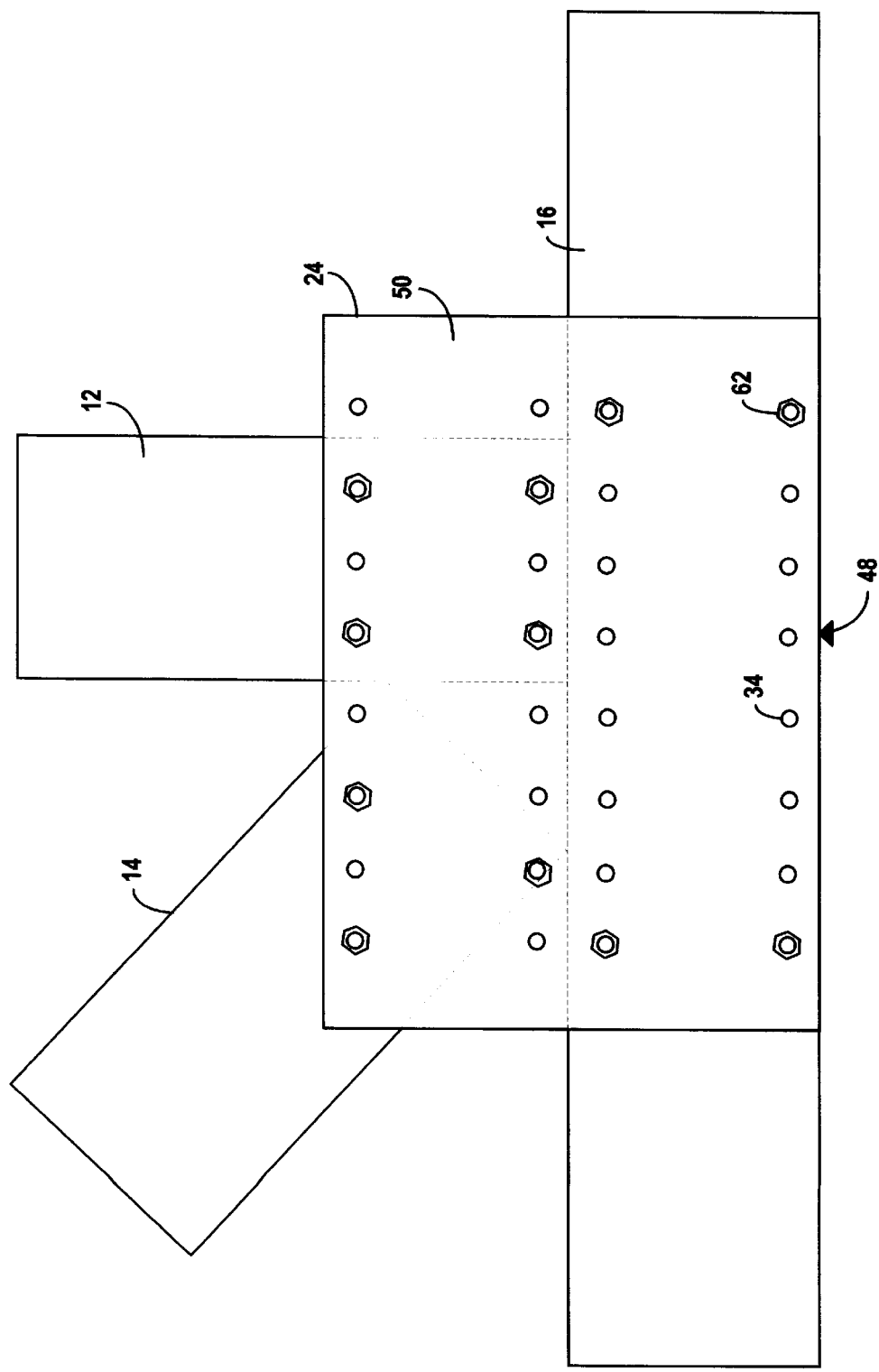
FIG. 12 is a detail view of a channel bracket.
Figure 13:
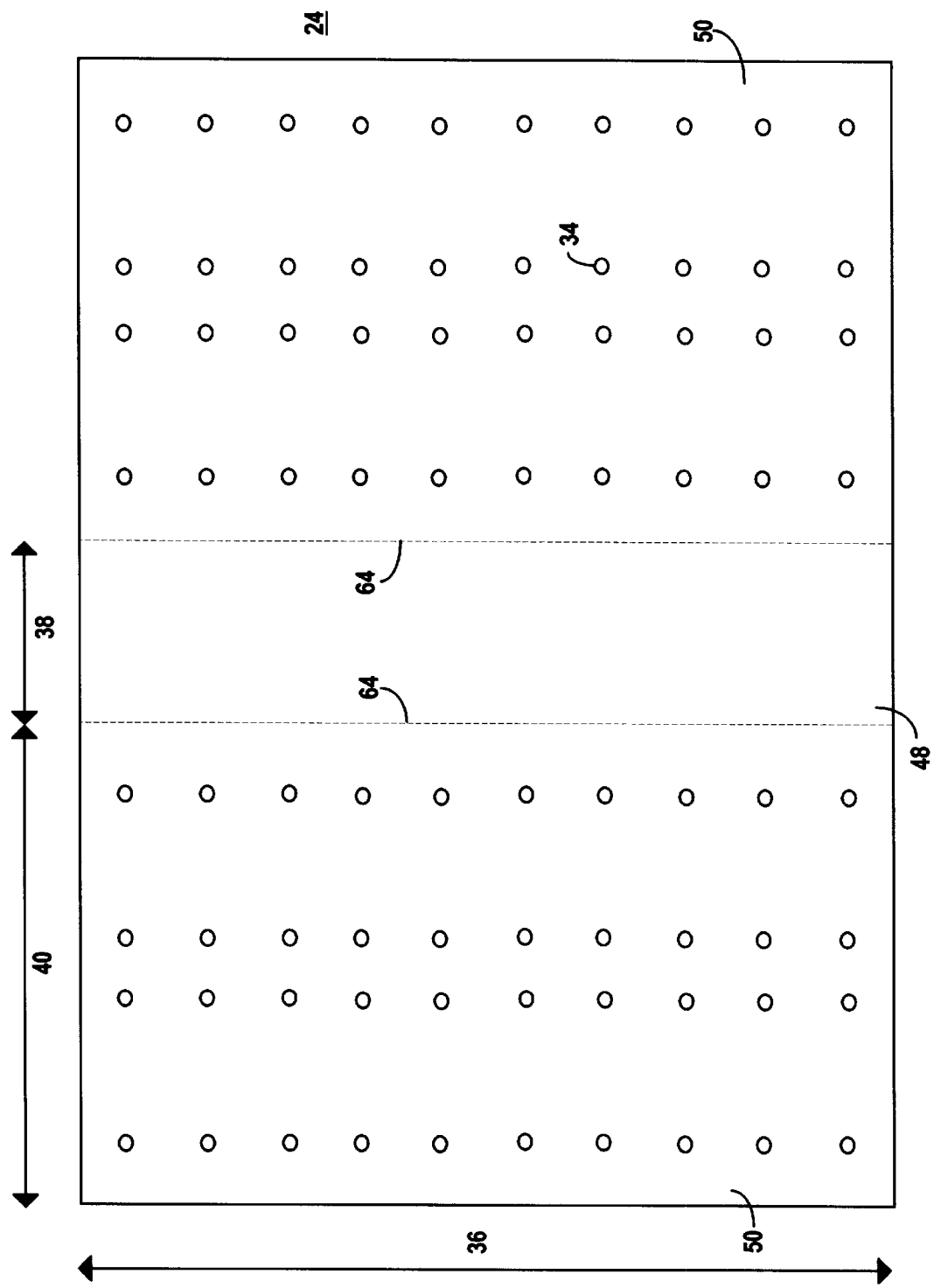
FIG. 13 is a dimensional view of a channel bracket.

FIG. 12 depicts the detail of a channel bracket 24, used to connect the ends of a compression web 12 and tension web 14 to either a ceiling joist 16 or rafter 10. Reference is also made to FIG. 13, which is a dimensional depiction of the channel bracket 24. The channel bracket 24 and its method of use will be most clearly understood during the following description by reference to both FIGS. 12 and 13. Channel bracket 24 has a spine 48, which is flanked on either side by two flaps 50. The flaps 50 are all folded up in the same direction at bend lines 64, so that the channel bracket 24 has a generally U shaped cross-section. The channel bracket 24 has a width 38, which is also the width of the spine 48, and which is designed to be substantially the same as the width 38 of the members which the channel bracket 24 is intended to connect together. The channel bracket 24 has a length 36, which is also the length of the flaps 50. As discussed above, in one embodiment the channel bracket 24 is pre-drilled with holes 34.

Although the channel bracket 24 can be used to connect both a compression web 12 and a tension web 14 to either a ceiling joist 16 or a rafter 10, or to connect two tension webs 14 to either the top chord 20 or bottom chord 56 of a floor joist 15, the example described herein will be that of connecting a compression web 12 and a tension web 14 to a ceiling joist 16. It will be appreciated that the method and manner or making the other connections is similar to that as described below.

The channel bracket 24 is connected to a position between the two ends of the ceiling joist 16, such that the end of the ceiling joist 16 is not inserted into the channel bracket 24. The ceiling joist 16 is inserted such that the spine 48 of the channel bracket 24 is disposed adjacent the width 38 of the ceiling joist 16. Thus, the two flaps 50 of the channel bracket 24 are disposed adjacent opposing sides of the ceiling joist 16. Steel fasteners, such as screws 62, are used to connect the channel bracket 24 to the stud 18. As discussed above, the screws 62 may be placed in the pre-drilled holes 34, or self-tapping screws 62 may be used and placed where desired, or a combination of both methods may be used.

Four screws 62 are preferably used to fasten each flap of the channel bracket 24 to the opposing sides of the ceiling joist 16, and one, two, or four screws 62 are preferably used to fasten the spine 48 of the channel bracket 24 to the face of the ceiling joist 16. Thus, regardless of the connection method used, as described above, there are at least four holes in each of the two connected flaps 50 that align with at least four holes in each side of the ceiling joist 16. In this manner, the channel bracket 24 is fastened on three side to the ceiling joist 16, thus providing a very strong connection to the ceiling joist 16.

The bottom ends of the compression web 12 and tension web 14 are inserted into the channel bracket 24, as depicted in FIG. 12, and connected to the channel bracket 24 in a manner similar to that described above. In this manner, the channel bracket 24 is securely connected at the flaps 50 to opposing exterior sides of the compression web 12 and the tension web 14.

The height 40 of the channel bracket 24 is preferably about twice the height 40 of the steel members used. Thus, if steel members having a height 40 of about three inches are used, then the height 40 of the channel bracket 24 is preferably about six inches. Similarly, if steel members having a height 40 of about six inches are used, then the height 40 of the channel bracket 24 is preferably about twelve inches. In the preferred embodiment, all of the various members used have the same height 40 and width 38. However, in alternate embodiments, the members are of different heights 40 or widths 38, and the brackets are adjusted accordingly. The length 36 of the channel bracket 24 is preferably about four times the height 40 of the members used.

Figure 14:
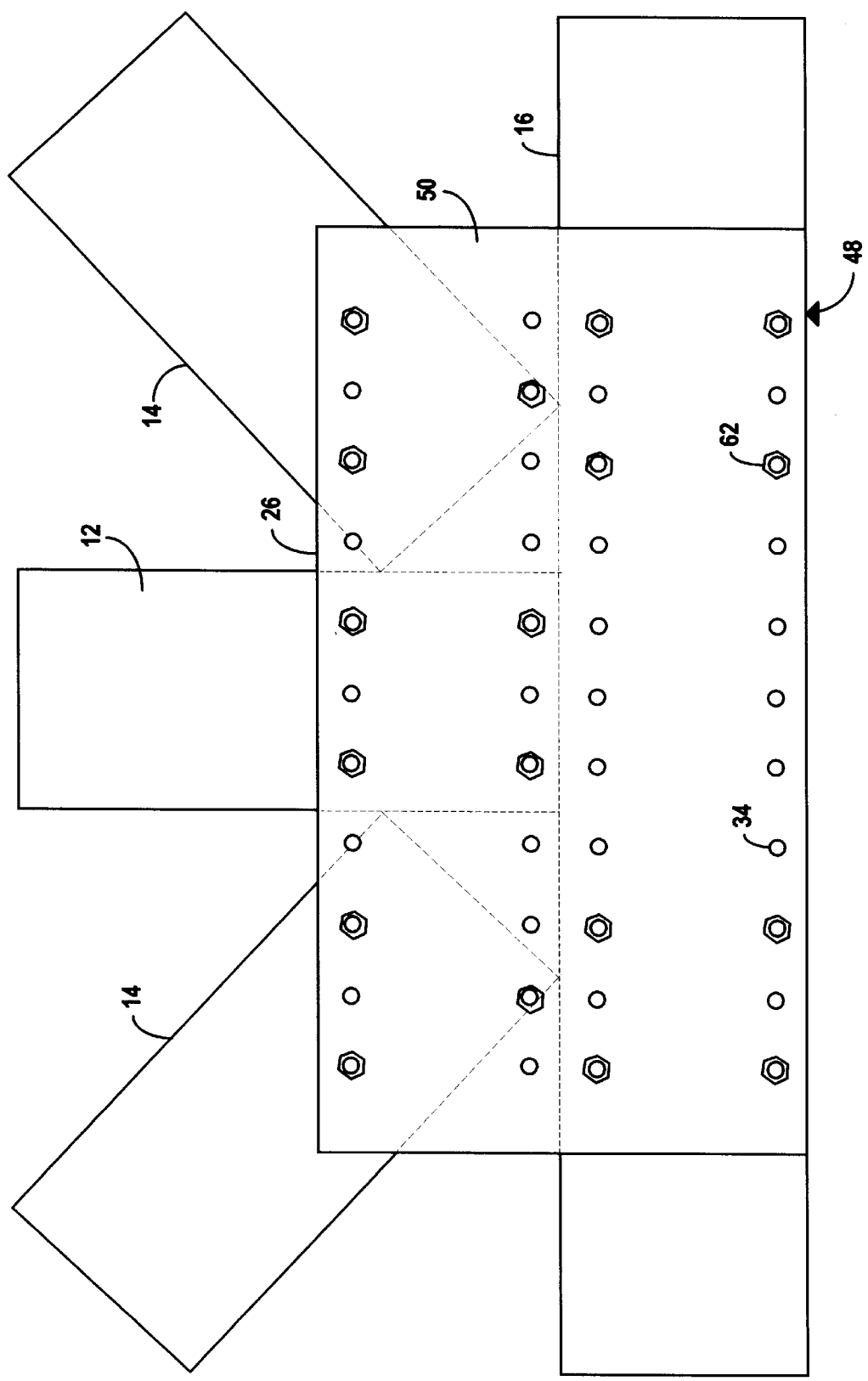
FIG. 14 is a detail view of a center bracket.
Figure 15:
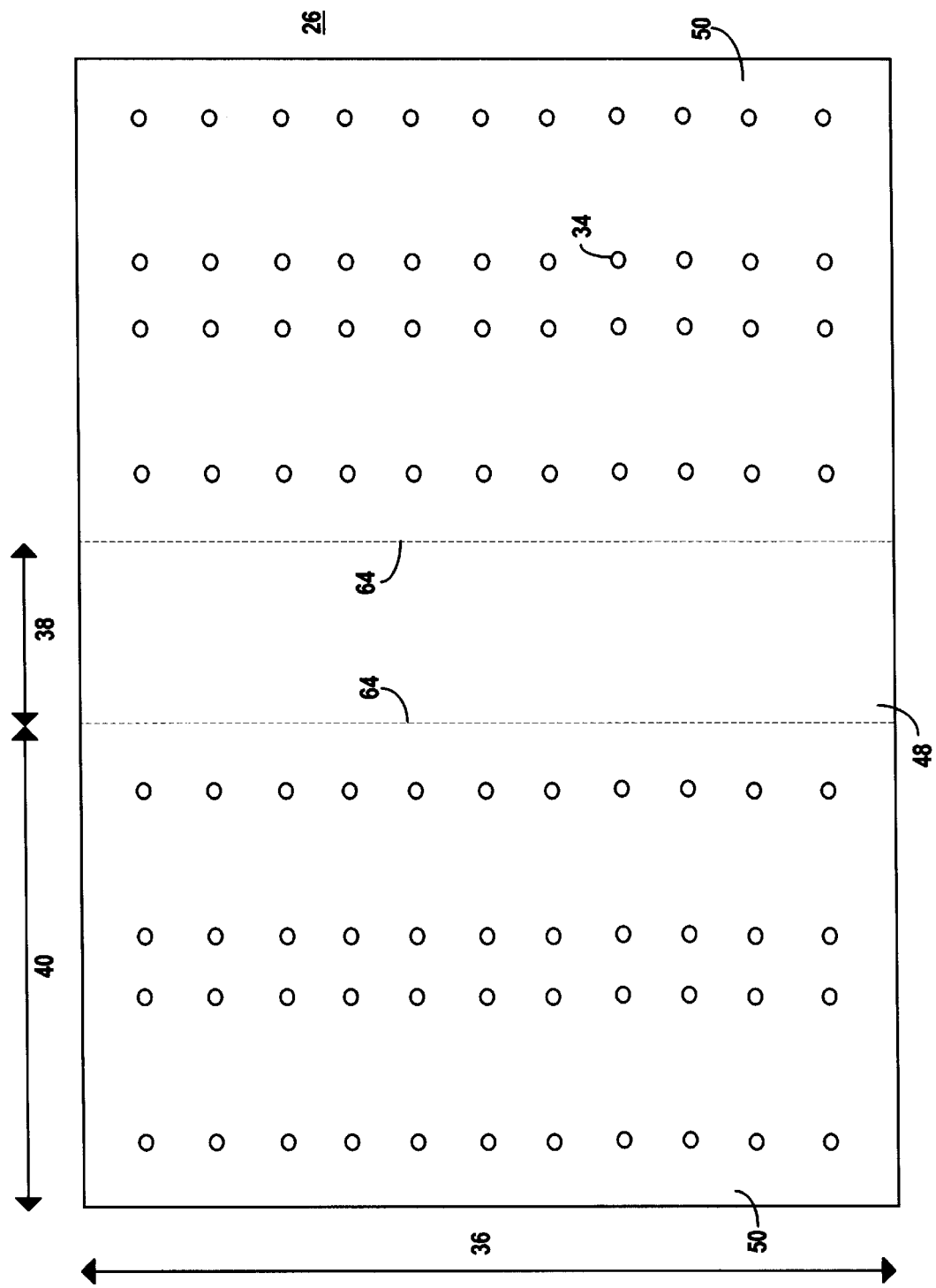
FIG. 15 is a dimensional view of a center bracket.

FIG. 14 depicts the detail of a center bracket 26, used to connect the ends of a compression web 12 and two tension webs 14 to either a ceiling joist 16 or a top chord 20. Reference is also made to FIG. 15, which is a dimensional depiction of the center bracket 26. The center bracket 26 and its method of use will be most clearly understood during the following description by reference to both FIGS. 14 and 15. Center bracket 26 has a spine 48, which is flanked on either side by flaps 50. The flaps 50 are folded up in the same direction at bend lines 64, so that the center bracket 26 has a generally U shaped cross-section. The center bracket 26 has a width 38, which is also the width of the spine 48, and which is designed to be substantially the same as the width 38 of the members which the center bracket 26 is intended to connect together. The center bracket 26 has a length 36, which is also the length of the flaps 50. As discussed above, in one embodiment the center bracket 26 is pre-drilled with holes 34.

Although the center bracket 26 can be used to connect a compression web 12 and two tension webs 14 to either a ceiling joist 16 or a top chord 20, the example described herein will be that of connecting a compression web 12 and two tension webs 14 to a ceiling joist 16. It will be appreciated that the method and manner or making the other connections is similar to that as described below.

The center bracket 26 is connected to a position midway between the two ends of the ceiling joist 16, such that either end of the ceiling joist 16 is not inserted into the center bracket 26. The ceiling joist 16 is inserted such that the spine 48 of the center bracket 26 is disposed adjacent the width 38 of the ceiling joist 16. Thus, the two flaps 50 of the center bracket 26 are disposed adjacent opposing sides of the ceiling joist 16. Steel fasteners, such as screws 62, are used to connect the center bracket 26 to the ceiling joist 16. As discussed above, the screws 62 may be placed in the pre-drilled holes 34, or self-tapping screws 62 may be used and placed where desired, or a combination of both methods may be used.

Eight screws 62 are preferably used to fasten each flap of the center bracket 26 to the opposing sides of the ceiling joist 16, and one, two, or four screws 62 are preferably used to fasten the spine 48 of the center bracket 26 to the face of the ceiling joist 16. Thus, regardless of the connection method used, as described above, there are at least eight holes in each of the two connected flaps 50 that align with at least eight holes in each side of the ceiling joist 16. In this manner, the center bracket 26 is fastened on three sides to the ceiling joist 16, thus providing a very strong connection to the ceiling joist 16.

The bottom ends of the compression web 12 and tension webs 14 are inserted into the center bracket 26, as depicted in FIG. 14, and connected to the center bracket 26 in a manner similar to that described above. In this manner, the center bracket 26 is securely connected at the flaps 50 to opposing exterior sides of the compression web 12 and the tension webs 14.

The height 40 of the center bracket 26 is preferably about twice the height 40 of the steel members used. Thus, if steel members having a height 40 of about three inches are used, then the height 40 of the center bracket 26 is preferably about six inches. Similarly, if steel members having a height 40 of about six inches are used, then the height 40 of the center bracket 26 is preferably about twelve inches. In the preferred embodiment, all of the various members used have the same height 40 and width 38. However, in alternate embodiments, the members are of different heights 40 or widths 38, and the brackets are adjusted accordingly. The length 36 of the center bracket 26 is preferably about four times the height 40 of the members used.

Figure 16:
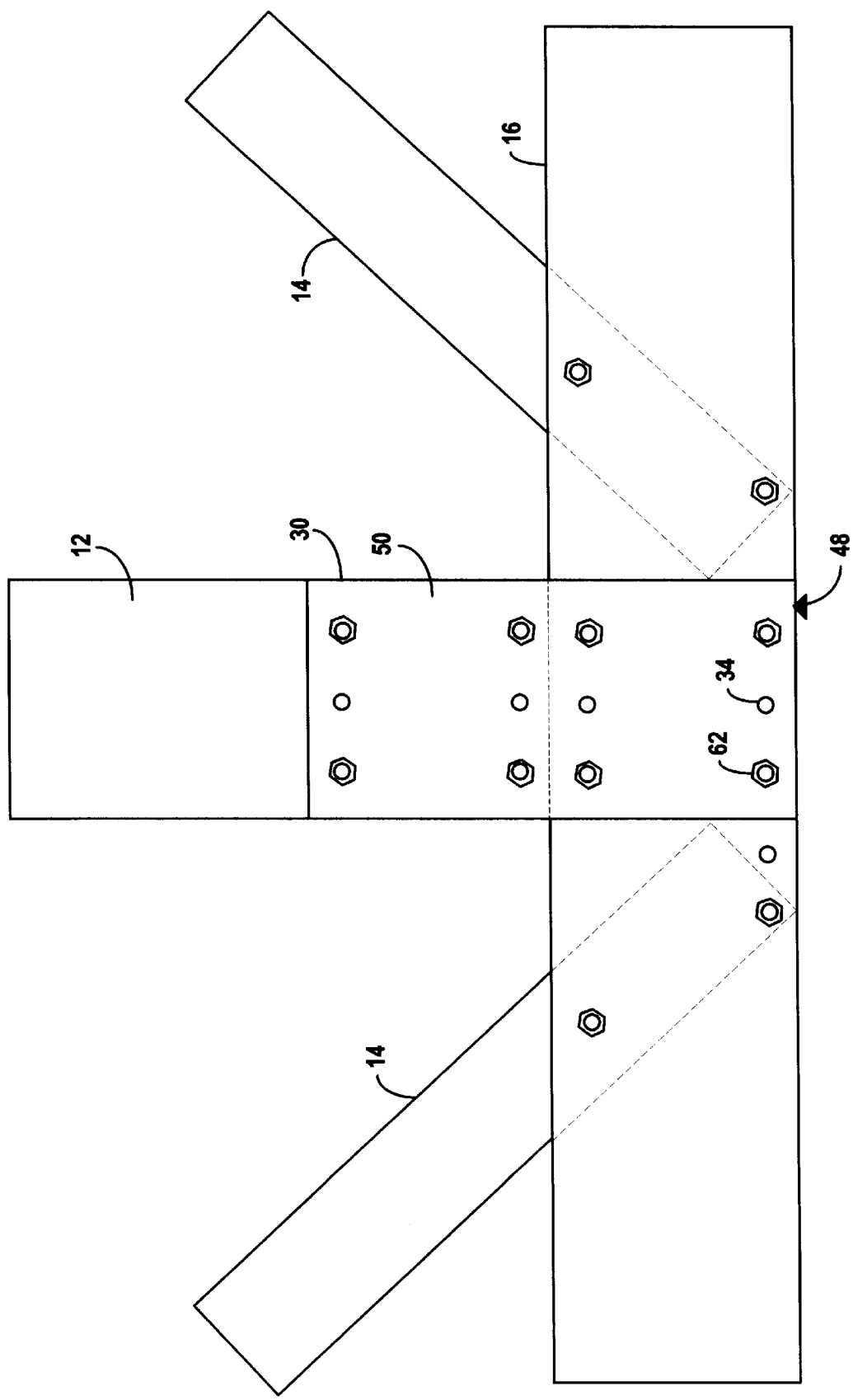
FIG. 16 is a detail view of a compression bracket.
Figure 17:
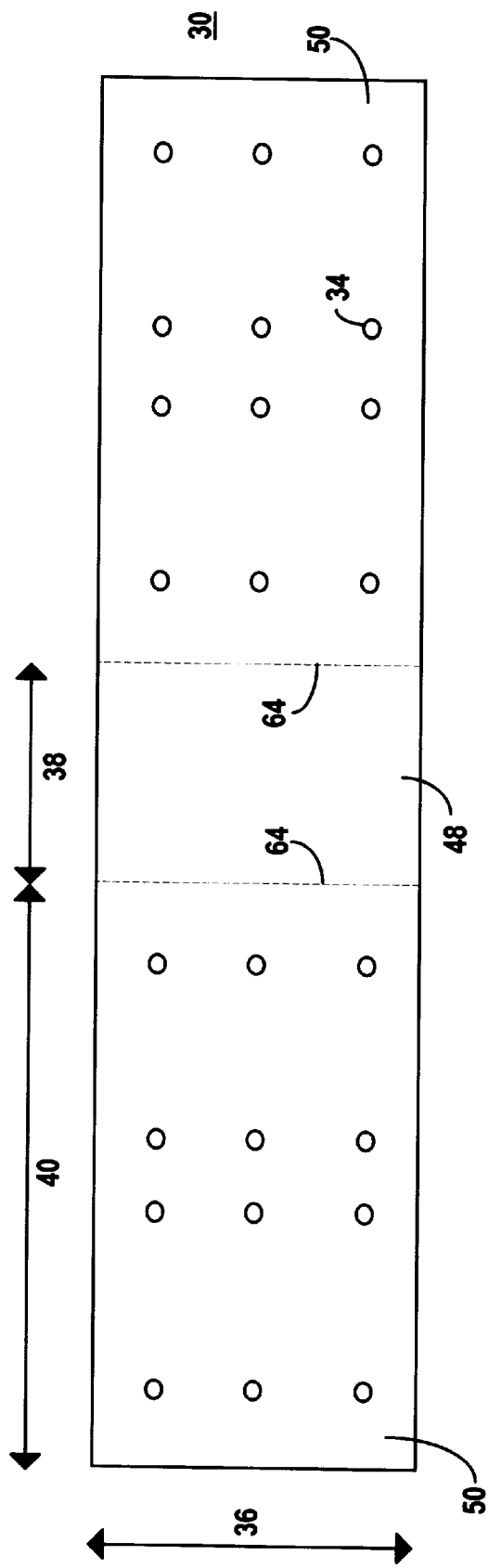
FIG. 17 is a dimensional view of a compression bracket.

FIG. 16 depicts the detail of a compression bracket 30, used to connect the end of a compression web 12 to either a ceiling joist 16 or a bottom chord 56. FIG. 16 also depicts another method of connecting members, which will be described in more detail below. Reference is also made to FIG. 17, which is a dimensional depiction of the compression bracket 30. The compression bracket 30 and its method of use will be most clearly understood during the following description by reference to both FIGS. 16 and 17. Compression bracket 30 has a spine 48, which is flanked on either side by flaps 50. The flaps 50 are folded up in the same direction at bend lines 64, so that the compression bracket 30 has a generally U shaped cross-section. The compression bracket 30 has a width 38, which is also the width of the spine 48, and which is designed to be substantially the same as the width 38 of the members which the compression bracket 30 is intended to connect together. The compression bracket 30 has a length 36, which is also the length of the flaps 50. As discussed above, in one embodiment the compression bracket 30 is pre-drilled with holes 34.

Although the compression bracket 30 can be used to connect a compression web 12 to either a ceiling joist 16 or a bottom chord 56, the example described herein will be that of connecting a compression web 12 to a ceiling joist 16. It will be appreciated that the method and manner or making the other connections is similar to that as described below.

The compression bracket 30 is connected to a position between the two ends of the ceiling joist 16, such that either end of the ceiling joist 16 is not inserted into the compression bracket 30. The ceiling joist 16 is inserted such that the spine 48 of the compression bracket 30 is disposed adjacent the width 38 of the ceiling joist 16. Thus, the two flaps 50 of the compression bracket 30 are disposed adjacent opposing sides of the ceiling joist 16. Steel fasteners, such as screws 62, are used to connect the compression bracket 30 to the ceiling joist 16. As discussed above, the screws 62 may be placed in the pre-drilled holes 34, or self-tapping screws 62 may be used and placed where desired, or a combination of both methods may be used.

Four screws 62 are preferably used to fasten each flap of the compression bracket 30 to the opposing sides of the ceiling joist 16, and one, two, or four screws 62 are preferably used to fasten the spine 48 of the compression bracket 30 to the face of the ceiling joist 16. Thus, regardless of the connection method used, as described above, there are at least four holes in each of the two connected flaps 50 that align with at least four holes in each side of the ceiling joist 16. In this manner, the compression bracket 30 is fastened on three sides to the ceiling joist 16, thus providing a very strong connection to the ceiling joist 16.

The bottom end of the compression web 12 is inserted into the compression bracket 30, as depicted in FIG. 16, and connected to the compression bracket 30 in a manner similar to that described above. In this manner, the compression bracket 30 is securely connected at the flaps 50 to opposing exterior sides of the compression web 12.

The height 40 of the compression bracket 30 is preferably about twice the height 40 of the steel members used. Thus, if steel members having a height 40 of about three inches are used, then the height 40 of the compression bracket 30 is preferably about six inches. Similarly, if steel members having a height 40 of about six inches are used, then the height 40 of the compression bracket 30 is preferably about twelve inches. In the preferred embodiment, all of the various members used have the same height 40 and width 38. However, in alternate embodiments, the members are of different heights 40 or widths 38, and the brackets are adjusted accordingly. The length 36 of the compression bracket 30 is preferably about the same as the width 38 of the members used.

Figure 18:
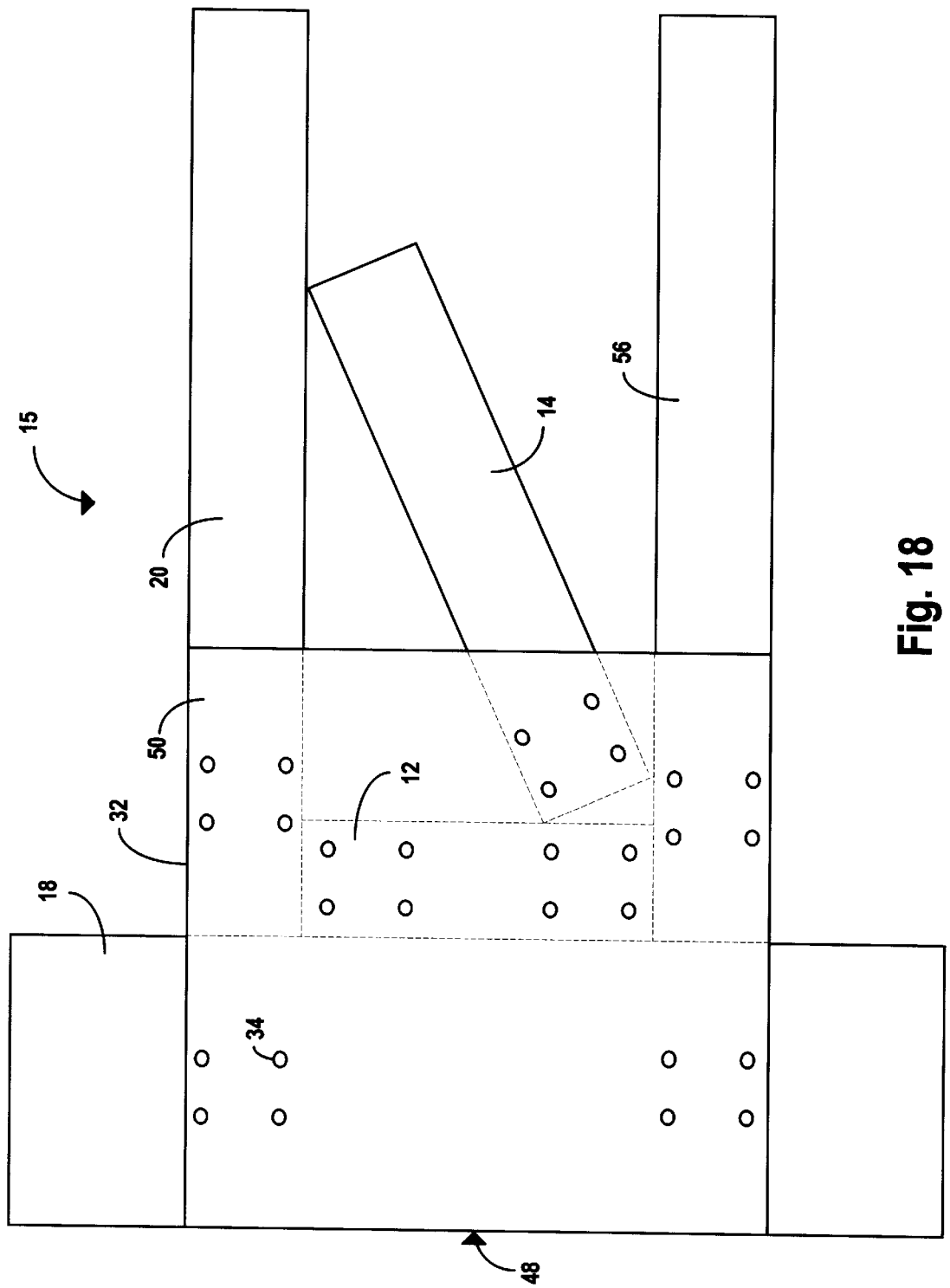
FIG. 18 is a detail view of a stud bracket.
Figure 19:
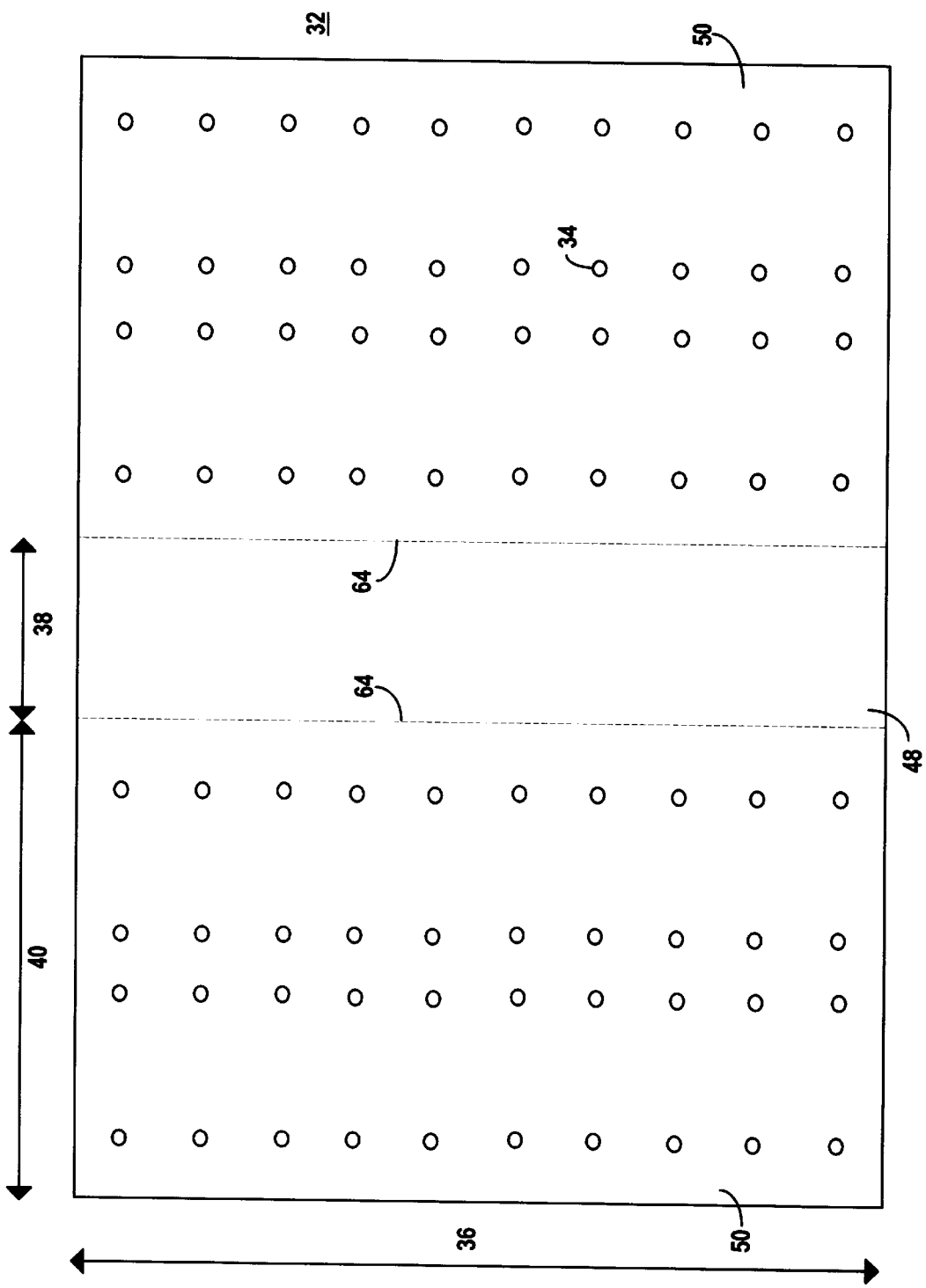
FIG. 19 is a dimensional view of a stud bracket.

FIG. 18 depicts the detail of a stud bracket 32, used to connect the end of a floor joist 15 to a stud 18. Reference is also made to FIG. 19, which is a dimensional depiction of the stud bracket 32. The stud bracket 32 and its method of use will be most clearly understood during the following description by reference to both FIGS. 18 and 19. Stud bracket 32 has a spine 48, which is flanked on either side by flaps 50. The flaps 50 are folded up in the same direction at bend lines 64, so that the stud bracket 32 has a generally U shaped cross-section. The stud bracket 32 has a width 38, which is also the width of the spine 48, and which is designed to be substantially the same as the width 38 of the members which the stud bracket 32 is intended to connect together. The stud bracket 32 has a length 36, which is also the length of the flaps 50. As discussed above, in one embodiment the stud bracket 32 is pre-drilled with holes 34.

The stud bracket 32 is connected to a position between the two ends of the stud 18, such that neither end of the stud 18 is inserted into the stud bracket 32. The stud 18 is inserted such that the spine 48 of the stud bracket 32 is disposed adjacent the width 38 of the stud 18. Thus, the two flaps 50 of the stud bracket 32 are disposed adjacent opposing sides of the stud 18. Steel fasteners, such as screws 62, are used to connect the stud bracket 32 to the stud 18. As discussed above, the screws 62 may be placed in the pre-drilled holes 34, or self-tapping screws 62 may be used and placed where desired, or a combination of both methods may be used.

Eight screws 62 are preferably used to fasten each flap of the stud bracket 32 to the opposing sides of the stud 18, and two, four, or eight screws 62 are preferably used to fasten the spine 48 of the stud bracket 32 to the face of the stud 18. Thus, regardless of the connection method used, as described above, there are at least eight holes in each of the two connected flaps 50 that align with at least eight holes in each side of the stud 18. In this manner, the stud bracket 32 is fastened on three sides to the stud 18, thus providing a very strong connection to the stud 18.

One end of the floor joist 15 is inserted into the stud bracket 32, as depicted in FIG. 18, and connected to the stud bracket 32 in a manner similar to that described above. In this manner, the stud bracket 32 is securely connected at the flaps 50 to opposing exterior sides of the floor joist 15.

The height 40 of the stud bracket 32 is preferably about twice the height 40 of the studs 18 used. Thus, if studs 18 having a height 40 of about three inches are used, then the height 40 of the stud bracket 32 is preferably about six inches. Similarly, if studs 18 having a height 40 of about six inches are used, then the height 40 of the stud bracket 32 is preferably about twelve inches. In the preferred embodiment, depicted in FIGS. 18 and 19, the studs 18 have heights 40 greater than that of the other members. However, in alternate embodiments, the members are of the same height 40, and the brackets are adjusted accordingly. The length 36 of the stud bracket 32 is preferably about twice the height 40 of the members used.

Thus, several methods of construction, including connecting members one to another, according to different embodiments of the invention have been described. The manner in which the different brackets are used has been explained with particularity, using specific examples. It will be appreciated that the brackets have utility beyond the specific examples. For example, in general, according to the invention, the adjustable brackets, such as the peak bracket, eave bracket, and slot bracket, are used to connect the ends of members to ends of other members. A compression bracket, stud bracket, or truss bracket is used to connect the end of one member to a mid point of another member. A channel bracket is used to connect the ends of two members to a mid point of another member. A center bracket is used to connect the ends of three members to a mid point of another member.

Figure 20:
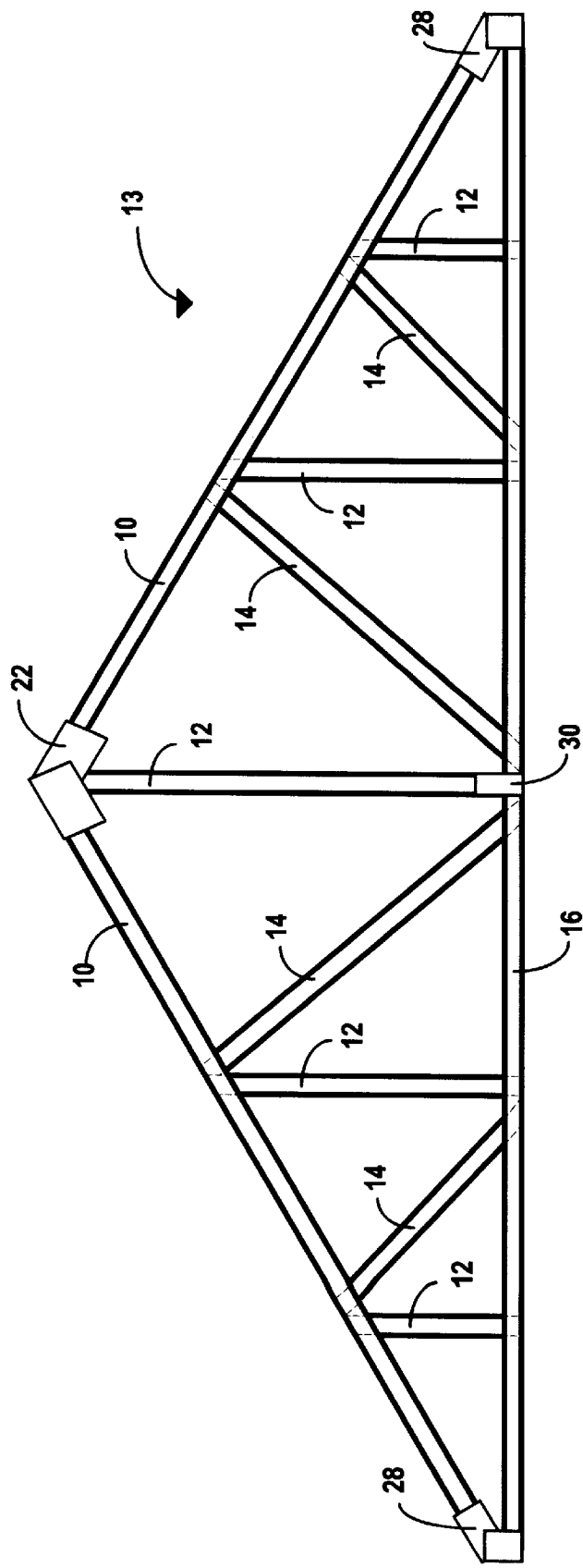
FIG. 20 depicts a slotted truss.
Figure 21:
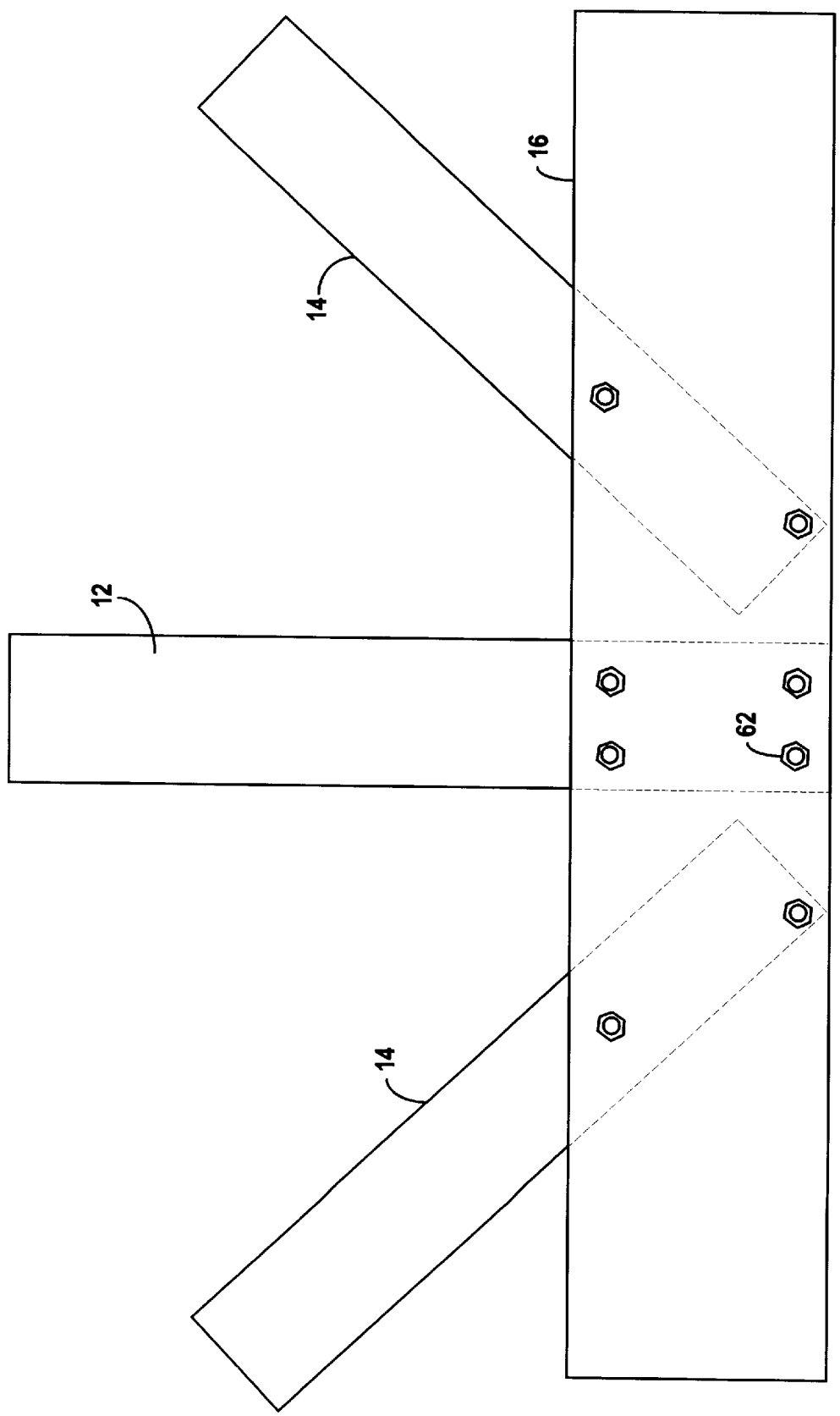
FIG. 21 is a detail view of slotted truss members.

FIG. 20 depicts a slotted truss 13 connected according to another embodiment of the invention. In this embodiment, the compression webs 12 and tension webs 14 are connected to the rafters 10 and the ceiling joist 16, not with brackets as described above, but by cutting slots in the rafters 10 and the ceiling joist 16, and fitting at least some of the compression webs 12 and tension webs 14 directly into the slots. Detail of such a connection method is depicted in FIG. 21. In FIG. 21, a compression web 12 and two tensions webs 14 are connected to a ceiling joist 16, in the region where a center bracket 26 would be used in the embodiment described at length above. However, in this alternate embodiment, no bracket is required. As can be seen, the compression web 12 and two tensions webs 14 fit within the ceiling joist 16, and are connected with fasteners, such as screws 62, directly to the ceiling joist 16.

Figure 22:
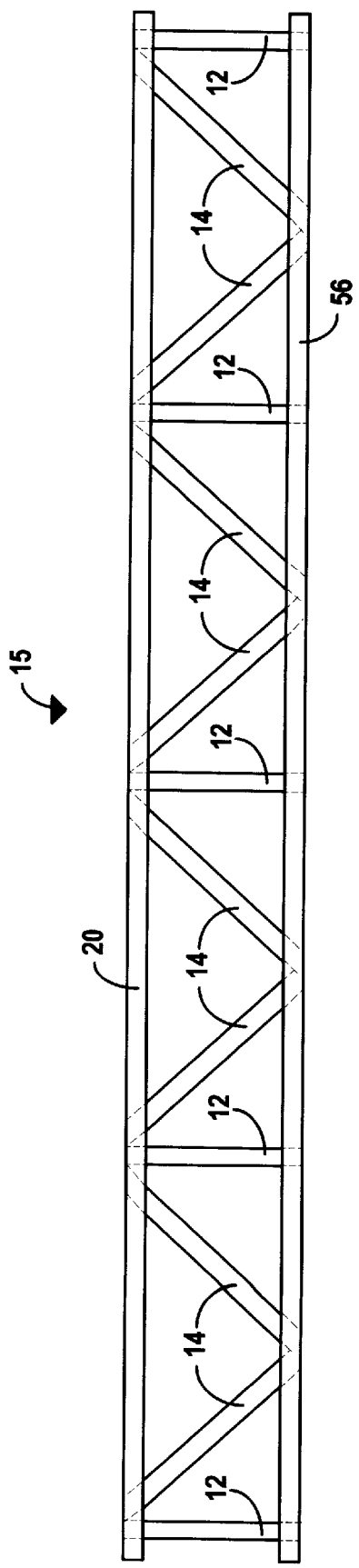
FIG. 22 depicts a slotted floor joist.

In the embodiment depicted, the rafters 10 and the ceiling joist 16 are made of C channel 52, and the compression web 12 and two tensions webs 14 are made of box channel 54. However, in alternate embodiments any or all of the members may be made of C channel 52, and any or all of the members may be made of box channel. FIG. 22 depicts a slotted floor joist 15 connected in the same manner as depicted in FIG. 20.

The connection methods of fitting members into slots and connecting members with brackets may also be blended in a third embodiment of the invention, as depicted in FIG. 16. In this example, the compression web 12 is formed of C channel 52 and attached to a C channel 52 ceiling joist 16 with a compression bracket 30. The two tension webs 14 are formed of box channel 54 and are attached to the C channel 52 ceiling joist 16 by inserting them into slots cut into the ceiling joist 16. All of the members are connected by fasteners, such as steel screws 62. In this manner, either C channel 52 or box channel 54 may be selected for a given member of the frame 11, depending on the design requirements, and the member may be connected by use of either a bracket or the slot insertion method described above.

It will be appreciated that the invention as described above comprehends adaptation, rearrangement, and substitution of parts, all of which would be considered to be within the scope and spirit of the invention as described, and that the scope of the invention is only to be restricted by the language of the claims given below.

What is claimed is:

1. A construction system for building a steel frame using steel members, comprising:

rafters formed of the steel members for forming a roof portion of the steel frame, a ceiling joist having two ends and formed of the steel members for forming a ceiling portion of the steel frame, compression webs formed of the steel members, the compression webs disposed between the rafters and the ceiling joists, for distributing load between the rafters and the ceiling joists, tension webs formed of the steel members, the tension webs disposed between the rafters, the ceiling joists, and the compression webs, for inhibiting distortion of the roof, a unitary peak bracket connecting two of the rafters at a variable roof pitch to one of the compression webs, the peak bracket connected to three outside surfaces on each of the two rafters and on two outside surfaces of the compression web, each of the two connected rafters thereby having a connected end and an unconnected end, the peak bracket having a length, width, and height, and also having a spine with four overlapping flaps adjacent the spine, the four flaps disposed at ninety degree angles from the spine, such that the four flaps and the spine have a cross-section generally resembling a U shape, the spine bendable to a variable degree at a position between the four flaps, at least one of the four flaps having alignment means on it, the alignment means calibrated in units that indicate the variable degree at which the spine is bent, the spine having a predetermined number of holes in it, and each flap having at least eight holes in it, the eight holes in each flap disposed such that four holes in each flap align with the compression web and one of the two connected rafters, eave brackets connecting the two unconnected ends of the two connected rafters to the ends of the ceiling joist, such that each end of the ceiling joist aligns with one of the unconnected ends of the two connected rafters, the eave brackets having a length, width, and height, and also having a spine with four flaps adjacent the spine, the four flaps disposed at ninety degree angles from the spine, such that the four flaps and the spine have a cross-section generally resembling a U shape, the spine bendable to a variable degree at a position between the four flaps, at least one of the four flaps having alignment means on it, the alignment means calibrated in units that indicate the variable degree at which the spine is bent, the spine having a predetermined number of holes in it, and each flap having at least four holes in it, the four holes in each flap disposed such that the four holes in each flap align with one of the ceiling joist and one of the two connected rafters, compression brackets connecting the compression webs to the ceiling joist, the compression brackets having a length, width, and height, and also having a spine with two flaps adjacent the spine, the two flaps disposed at ninety degree angles from the spine, such that the two flaps and the spine have a cross-section generally resembling a U shape, the spine having a predetermined number of holes in it, and each flap having at least eight holes in it, the eight holes in each flap disposed such that four holes in each flap align with each of the connected compression web and the ceiling joist, a center bracket connecting two of the tension webs and one of the compression webs to the ceiling joist, the center bracket having a length, width, and height, and also having a spine with two flaps adjacent the spine, the two flaps disposed at ninety degree angles from the spine, such that the two flaps and the spine have a cross-section generally resembling a U shape, the spine having a predetermined number of holes in it, and each flap having at least sixteen holes in it, the sixteen holes in each flap disposed such that at least four holes in each flap align with each of the connected compression web, the two tension webs, and the ceiling joist, and channel brackets connecting one of the tension webs and one of the compression webs to one of the rafters and the ceiling joist, the channel brackets having a length, width, and height, and also having a spine with two flaps adjacent the spine, the two flaps disposed at ninety degree angles from the spine, such that the two flaps and the spine have a cross-section generally resembling a U shape, the spine having a predetermined number of holes in it, and each flap having at least twelve holes in it, the twelve holes in each flap disposed such that four holes in each flap align with each of the connected compression web, tension web, and one of the rafter and ceiling joist.

2. The construction system of claim 1, further comprising:

studs formed of the steel members for forming a wall portion of the frame, and truss brackets connecting two of the studs to the ceiling joist, the truss brackets having a length, width, and height, and also having a spine with four flaps adjacent the spine, the four flaps disposed at ninety degree angles from the spine, such that the four flaps and the spine have a cross-section generally resembling a U shape, the spine of the truss brackets bendable to ninety degrees, such that when the spine is bent adjacent edges of adjacent flaps are also disposed at ninety degrees one to the other, the spine having a predetermined number of holes in it, and each flap having at least four holes in it, the four holes in each flap disposed such that the four holes in each flap align with one of the ceiling joist and one of the connected studs.

3. The construction system of claim 2, further comprising:

a floor joist having a height, and formed of the steel members, the floor joist for forming a floor portion of the steel frame, and stud brackets connecting two of the studs to the floor joist, the stud brackets having a length, width, and height, and also having a spine with two flaps adjacent the spine, the two flaps disposed at ninety degree angles from the spine, such that the two flaps and the spine have a cross-section generally resembling a U shape, the spine having a predetermined number of holes in it, and each flap having at least sixteen holes in it, the sixteen holes in each flap disposed such that eight holes in each flap align with each of the connected stud and the floor joist.

4. The construction system of claim 3 wherein the alignment means of the peak bracket and eave brackets further comprise scoring marks, such that when the spine is bent an edge of an adjacent one of the four flaps is alignable to the scoring marks.

5. The construction system of claim 3 wherein the alignment means of the peak bracket and eave brackets further comprise holes, such that when the spine is bent the holes in one of the four flaps are alignable to the holes in an adjacent one of the four flaps.

6. The construction system of claim 3 wherein the peak bracket, the channel bracket, the eave brackets, the center brackets, the compression brackets, the truss brackets, and the stud brackets are formed of steel.

7. The construction system of claim 3 wherein the width of the peak bracket, the channel bracket, the eave brackets, the center brackets, the compression brackets, the truss brackets, and the stud brackets is about two inches.

8. The construction system of claim 3 wherein the width of the peak bracket, the channel bracket, the eave brackets, the center brackets, the compression brackets, the truss brackets, and the stud brackets is about 1.75 inches.

9. The construction system of claim 3 wherein the length and height of the peak bracket is about twelve inches and about fifteen inches, respectively.

10. The construction system of claim 3 wherein the length and height of the channel brackets is about six inches and about nine inches, respectively.

11. The construction system of claim 3 wherein the length and height of the eave brackets is about six inches and about six inches, respectively.

12. The construction system of claim 3 wherein the length and height of the center brackets is about twelve inches and about twelve inches, respectively.

13. The construction system of claim 3 wherein the length and height of the compression brackets is about three inches and about nine inches, respectively.

14. The construction system of claim 3 wherein the length and height of the stud brackets is about the height of the floor joist and about twelve inches, respectively.

15. The construction system of claim 3 wherein the units in which the scoring marks on the peak bracket are calibrated are degrees.

16. The construction system of claim 3 wherein the units in which the scoring marks on the peak bracket are calibrated are roof pitch.

17. The construction system of claim 3 wherein the predetermined number of holes in the spine of the peak bracket, the channel bracket, the center brackets, the compression brackets, the truss brackets, and the stud brackets is one per said steel member adjacent the spine.

18. The construction system of claim 3 wherein the predetermined number of holes in the spine of the peak bracket, the channel bracket, the center brackets, the compression brackets, the truss brackets, and the stud brackets is two per said steel member adjacent the spine.

19. The construction system of claim 3 wherein the predetermined number of holes in the spine of the peak bracket, the channel bracket, the center brackets, the compression brackets, the truss brackets, and the stud brackets is four per said steel member adjacent the spine.

20. The construction system of claim 3 wherein the steel members further comprise C channel.

21. A construction system for building a steel frame using steel members constructed of C channel, comprising:

rafters formed of the steel C channel members for forming a roof portion of the steel frame, a ceiling joist having two ends and formed of the steel C channel members for forming a ceiling portion of the steel frame, studs formed of the steel C channel members for forming a wall portion of the steel frame, a floor joist having a height, and formed of the steel C channel members, the floor joist for forming a floor portion of the steel frame, compression webs formed of the steel C channel members, the compression webs disposed between the rafters and the ceiling joists, for distributing load between the rafters and the ceiling joists, tension webs formed of the steel C channel members, the tension webs disposed between the rafters, the ceiling joists, and the compression webs, for inhibiting distortion of the roof, a unitary peak bracket connecting two of the rafters at a variable roof pitch to one of the compression webs, the peak bracket connected to three outside surfaces on each of the two rafters and on two outside surfaces of the compression web, each of the two connected rafters thereby having a connected end and an unconnected end, the peak bracket having a length, width, and height, and also having a spine with four overlapping flaps adjacent the spine, the four flaps disposed at ninety degree angles from the spine, such that the four flaps and the spine have a cross-section generally resembling a U shape, the spine bendable to a variable degree at a position between the four flaps, at least one of the four flaps having scoring marks on it, such that when the spine is bent an edge of an adjacent one of the four flaps is alignable to the scoring marks, the scoring marks calibrated in units that indicate the variable degree at which the spine is bent, the spine having at least four holes in it, the four holes in the spine disposed such that two holes in the spine align with each of the two connected rafters, and each flap having at least eight holes in it, the eight holes in each flap disposed such that four holes in each flap align with the compression web and one of the two connected rafters, eave brackets connecting the two unconnected ends of the two connected rafters to the ends of the ceiling joist, such that each end of the ceiling joist aligns with one of the unconnected ends of the two connected rafters, the eave brackets having a length, width, and height, and also having a spine with four flaps adjacent the spine, the four flaps disposed at ninety degree angles from the spine, such that the four flaps and the spine have a cross-section generally resembling a U shape, the spine bendable to a variable degree at a position between the four flaps, at least one of the four flaps having scoring marks on it, such that when the spine is bent an edge of an adjacent one of the four flaps is alignable to the scoring marks, the scoring marks calibrated in units that indicate the variable degree at which the spine is bent, the spine having at least two holes in it, the two holes in the spine disposed such that the two holes in the spine align with one of the two connected rafters, and each flap having at least four holes in it, the four holes in each flap disposed such that the four holes in each flap align with one of the ceiling joist and the two connected rafters, compression brackets connecting the compression webs to the ceiling joist, the compression brackets having a length, width, and height, and also having a spine with two flaps adjacent the spine, the two flaps disposed at ninety degree angles from the spine, such that the two flaps and the spine have a cross-section generally resembling a U shape, the spine having at least two holes in it, and each flap having at least eight holes in it, the eight holes in each flap disposed such that four holes in each flap align with each of the connected compression webs and the ceiling joist, a center bracket connecting two of the tension webs and one of the compression webs to the ceiling joist, the center bracket having a length, width, and height, and also having a spine with two flaps adjacent the spine, the two flaps disposed at ninety degree angles from the spine, such that the two flaps and the spine have a cross-section generally resembling a U shape, the spine having at least two holes in it, and each flap having at least sixteen holes in it, the sixteen holes in each flap disposed such that at least four holes in each flap align with each of the connected compression web, the two tension webs, and the ceiling joist, channel brackets connecting one of the tension webs and one of the compression webs to one of the rafters and the ceiling joist, the channel brackets having a length, width, and height, and also having a spine with two flaps adjacent the spine, the two flaps disposed at ninety degree angles from the spine, such that the two flaps and the spine have a cross-section generally resembling a U shape, the spine having at least two holes in it, and each flap having at least twelve holes in it, the twelve holes in each flap disposed such that four holes in each flap align with each of the connected compression web, tension web, and one of the rafter and ceiling joist, truss brackets connecting two of the studs to the ceiling joist, the truss brackets having a length, width, and height, and also having a spine with four flaps adjacent the spine, the four flaps disposed at ninety degree angles from the spine, such that the four flaps and the spine have a cross-section generally resembling a U shape, the spine of the truss brackets bendable to ninety degrees, such that when the spine is bent adjacent edges of adjacent flaps are also disposed at ninety degrees one to the other, the spine having at least two holes in it, the two holes in the spine disposed such that the two holes in the spine align with one of the two connected rafters, and each flap having at least four holes in it, the four holes in each flap disposed such that the four holes in each flap align with one of the ceiling joist and one of the connected studs, stud brackets connecting two of the studs to the floor joist, the stud brackets having a length, width, and height, and also having a spine with two flaps adjacent the spine, the two flaps disposed at ninety degree angles from the spine, such that the two flaps and the spine have a cross-section generally resembling a U shape, the spine having at least four holes in it, and each flap having at least sixteen holes in it, the sixteen holes in each flap disposed such that eight holes in each flap align with each of the connected studs and the floor joist.

22. A construction system for building a steel frame using steel members, comprising:

rafters formed of the steel members for forming a roof portion of the steel frame, a ceiling joist having two ends and formed of the steel members for forming a ceiling portion of the steel frame, adjustable brackets, each of the adjustable brackets having a length, width, and height, and also having a spine with four overlapping flaps adjacent the spine, the four flaps disposed at ninety degree angles from the spine, such that the four flaps and the spine have a cross-section generally resembling a U shape, the spine bendable to a variable degree at a position between the four flaps, at least one of the four flaps having scoring marks on it, such that when the spine is bent in a first direction an edge of an adjacent one of the four flaps is alignable to the scoring marks, the scoring marks calibrated in units that indicate the variable degree at which the spine is bent, the spine having a predetermined number of holes in it, and each flap having at least four holes in it, a first of the adjustable brackets bent in the first direction to a first desired variable degree, the first adjustable bracket connecting two of the rafters together at a variable roof pitch, the first adjustable bracket connected to three outside surfaces on each of the two rafters, each of the two connected rafters thereby having a connected end and an unconnected end, the four holes in each flap of the first adjustable bracket disposed such that the four holes in each flap align with one of the two connected rafters, and a second and a third of the adjustable brackets bent in the first direction to a second desired variable degree, the second and third adjustable brackets connecting the two unconnected ends of the two connected rafters to the ends of the ceiling joist, such that each end of the ceiling joist aligns with one of the unconnected ends of the two connected rafters, the four holes in each flap of the second and the third adjustable brackets disposed such that the four holes in each flap align with one of the ceiling joist and the connected rafters.

23. The construction system of claim 22 further comprising:

studs formed of the steel members for forming a wall portion of the frame, and a fourth and a fifth of the adjustable brackets bent in a direction opposite the first direction to a ninety degree angle, the fourth and fifth adjustable brackets connecting two of the studs to the ceiling joist.

24. The construction system of claim 22 further comprising:

compression webs formed of the steel members, the compression webs disposed between the rafters and the ceiling joists, for distributing load between the rafters and the ceiling joists, tension webs formed of the steel members, the tension webs disposed between the rafters, the ceiling joists, and the compression webs, for inhibiting distortion of the roof, and channel brackets connecting at least one of the tension webs and one of the compression webs to one of the rafters and the ceiling joist, each of the channel brackets having a length, width, and height, and also having a spine with two flaps adjacent the spine, the two flaps disposed at ninety degree angles from the spine, such that the two flaps and the spine have a cross-section generally resembling a U shape, the spine having a predetermined number of holes in it, and each flap having at least twelve holes in it, the twelve holes in each flap disposed such that four holes in each flap align with each of the connected compression web, tension web, and one of the rafter and ceiling joist.

25. The construction system of claim 24 wherein the first, second, third, fourth, and fifth adjustable brackets are substantially identical in length.

26. The construction system of claim 24 wherein all of the channel brackets are substantially identical in length.

27. The construction system of claim 24 wherein the steel members further comprise C channel.

28. The construction system of claim 24 wherein the steel members further comprise box channel.

29. The construction system of claim 24 wherein the steel members further comprise C channel and box channel.

30. A construction system for building a steel frame using steel members, comprising:

rafters formed of the steel members for forming a roof portion of the steel frame, a ceiling joist having two ends and formed of the steel members for forming a ceiling portion of the steel frame, studs formed of the steel members for forming a wall portion of the steel frame, and compression webs formed of the steel members, the compression webs disposed between the rafters and the ceiling joists, for distributing load between the rafters and the ceiling joists, tension webs formed of the steel members, the tension webs disposed between the rafters, the ceiling joists, and the compression webs, for inhibiting distortion of the roof, adjustable brackets, each of the adjustable brackets having a length, width, and height, and also having a spine with four overlapping flaps adjacent the spine, the four flaps disposed at ninety degree angles from the spine, such that the four flaps and the spine have a cross-section generally resembling a U shape, the spine bendable to a variable degree at a position between the four flaps, at least one of the four flaps having scoring marks on it, such that when the spine is bent in a first direction an edge of an adjacent one of the four flaps is alignable to the scoring marks, the scoring marks calibrated in units that indicate the variable degree at which the spine is bent, the spine having a predetermined number of holes in it, and each flap having at least four holes in it, a first of the adjustable brackets bent in the first direction to a first desired variable degree, the first adjustable bracket connecting two of the rafters together at a variable roof pitch, the first adjustable bracket connected to three outside surfaces on each of the two rafters, each of the two connected rafters thereby having a connected end and an unconnected end, the four holes in each flap of the first adjustable bracket disposed such that the four holes in each flap align with one of the two connected rafters, and a second and a third of the adjustable brackets bent in the first direction to a second desired variable degree, the second and third adjustable brackets connecting the two unconnected ends of the two connected rafters to the ends of the ceiling joist, such that each end of the ceiling joist aligns with one of the unconnected ends of the two connected rafters, the four holes in each flap of the second and the third adjustable brackets disposed such that the four holes in each flap align with one of the ceiling joist and the connected rafters, a fourth and a fifth of the adjustable brackets bent in a direction opposite the first direction to a ninety degree angle, the fourth and fifth adjustable brackets connecting two of the studs to the ceiling joist, and channel brackets connecting at least one of the tension webs and one of the compression webs to one of the rafters and the ceiling joist, each of the channel brackets having a length, width, and height, and also having a spine with two flaps adjacent the spine, the two flaps disposed at ninety degree angles from the spine, such that the two flaps and the spine have a cross-section generally resembling a U shape, the spine having a predetermined number of holes in it, and each flap having at least twelve holes in it, the twelve holes in each flap disposed such that four holes in each flap align with each of the connected compression web, tension web, and one of the rafter and ceiling joist.

31. The construction system of claim 30 wherein the first, second, third, fourth, and fifth adjustable brackets are substantially identical in length.

32. The construction system of claim 30 wherein all of the channel brackets are substantially identical in length.

33. The construction system of claim 30 wherein the steel members further comprise C channel.

34. The construction system of claim 30 wherein the steel members further comprise box channel.

35. The construction system of claim 30 wherein the steel members further comprise C channel and box channel.

36. A construction system for building a steel frame using steel members, comprising:

rafters formed of the steel members for forming a roof portion of the steel frame, ceiling joists having two ends and formed of the steel members for forming a ceiling portion of the steel frame, compression webs formed of the steel members, the compression webs disposed between the rafters and the ceiling joists, for distributing load between the rafters and the ceiling joists, tension webs formed of the steel members, the tension webs disposed between the rafters, the ceiling joists, and the compression webs, for inhibiting distortion of the roof, a unitary peak bracket connecting two rafters at a variable roof pitch to a compression web, the peak bracket connected to three outside surfaces on each of the two rafters and on two outside surfaces of the compression web, each of the two connected rafters thereby having a connected end and an unconnected end, the peak bracket having a length, width, and height, and also having a spine with four overlapping flaps adjacent the spine, the four flaps disposed at ninety degree angles from the spine, such that the four flaps and the spine have a cross-section generally resembling a U shape, the spine bendable to a variable degree at a position between the four flaps, at least one of the four flaps having alignment means on it, the alignment means calibrated in units that indicate the variable degree at which the spine is bent, the spine having a predetermined number of holes in it, and each flap having at least eight holes in it, the eight holes in each flap disposed such that four holes in each flap align with the compression web and one of the two connected rafters, eave brackets connecting the two unconnected ends of the two connected rafters to one of the ends of each of the ceiling joists, such that each of the connected ends of the ceiling joists aligns with one of the unconnected ends of the two connected rafters, the eave brackets having a length, width, and height, and also having a spine with four flaps adjacent the spine, the four flaps disposed at ninety degree angles from the spine, such that the four flaps and the spine have a cross-section generally resembling a U shape, the spine bendable to a variable degree at a position between the four flaps, at least one of the four flaps having alignment means on it, the alignment means calibrated in units that indicate the variable degree at which the spine is bent, the spine having a predetermined number of holes in it, and each flap having at least four holes in it, the four holes in each flap disposed such that the four holes in each flap align with one of either one of the two ceiling joists and one of the two connected rafters, compression brackets connecting the compression webs to one of the ceiling joists, the compression brackets having a length, width, and height, and also having a spine with two flaps adjacent the spine, the two flaps disposed at ninety degree angles from the spine, such that the two flaps and the spine have a cross-section generally resembling a U shape, the spine having a predetermined number of holes in it, and each flap having at least eight holes in it, the eight holes in each flap disposed such that four holes in each flap align with each of the connected compression web and the ceiling joist, slot brackets connecting two of the tension webs and one of the compression webs to the unconnected ends of the two ceiling joists at a variable degree, the slot brackets having a length, width, and height, and also having a spine with two flaps adjacent the spine, the two flaps disposed at ninety degree angles from the spine, such that the two flaps and the spine have a cross-section generally resembling a U shape, at least one of the two flaps having alignment means on it, the alignment means calibrated in units that indicate the variable degree at which the ceiling joists are connected, the spine having a predetermined number of holes in it, and each flap having at least four holes in it, the four holes in each flap disposed such that the four holes in each flap align with the connected ceiling joist, and channel brackets connecting one of the tension webs and one of the compression webs to one of the rafters and the ceiling joists, the channel brackets having a length, width, and height, and also having a spine with two flaps adjacent the spine, the two flaps disposed at ninety degree angles from the spine, such that the two flaps and the spine have a cross-section generally resembling a U shape, the spine having a predetermined number of holes in it, and each flap having at least twelve holes in it, the twelve holes in each flap disposed such that four holes in each flap align with each of the connected compression web, tension web, and one of the rafter and ceiling joists.

37. The construction system of claim 36, further comprising:

studs formed of the steel members for forming a wall portion of the frame, and truss brackets connecting two of the studs to the ceiling joists, the truss brackets having a length, width, and height, and also having a spine with four flaps adjacent the spine, the four flaps disposed at ninety degree angles from the spine, such that the four flaps and the spine have a cross-section generally resembling a U shape, the spine of the truss brackets bendable to ninety degrees, such that when the spine is bent adjacent edges of adjacent flaps are also disposed at ninety degrees one to the other, the spine having a predetermined number of holes in it, and each flap having at least four holes in it, the four holes in each flap disposed such that the four holes in each flap align with one of the ceiling joists and one of the connected studs.

38. The construction system of claim 37, further comprising:

a floor joist having a height, and formed of the steel members, the floor joist for forming a floor portion of the steel frame, and stud brackets connecting two of the studs to the floor joist, the stud brackets having a length, width, and height, and also having a spine with two flaps adjacent the spine, the two flaps disposed at ninety degree angles from the spine, such that the two flaps and the spine have a cross-section generally resembling a U shape, the spine having a predetermined number of holes in it, and each flap having at least sixteen holes in it, the sixteen holes in each flap disposed such that eight holes in each flap align with each of the connected stud and the floor joist.

39. The construction system of claim 38 wherein the alignment means of the peak bracket, slot brackets, and eave brackets further comprise scoring marks, such that when the spine of the peak bracket and eave bracket is bent an edge of an adjacent one of the four flaps is alignable to the scoring marks.

40. The construction system of claim 38 wherein the alignment means of the peak bracket, slot brackets, and eave brackets further comprise holes, such that when the spine of the peak bracket and eave brackets is bent the holes in one of the four flaps are alignable to the holes in an adjacent one of the four flaps.

41. The construction system of claim 38 wherein the peak bracket, the channel bracket, the eave brackets, the slot brackets, the compression brackets, the truss brackets, and the stud brackets are formed of steel.

42. The construction system of claim 38 wherein the width of the peak bracket, the channel bracket, the eave brackets, the slot brackets, the compression brackets, the truss brackets, and the stud brackets is about two inches.

43. The construction system of claim 38 wherein the width of the peak bracket, the channel bracket, the eave brackets, the slot brackets, the compression brackets, the truss brackets, and the stud brackets is about 1.75 inches.

44. The construction system of claim 38 wherein the length and height of the peak bracket is about twelve inches and about fifteen inches, respectively.

45. The construction system of claim 38 wherein the length and height of the channel brackets is about six inches and about nine inches, respectively.

46. The construction system of claim 38 wherein the length and height of the eave brackets is about six inches and about six inches, respectively.

47. The construction system of claim 38 wherein the length and height of the compression brackets is about three inches and about nine inches, respectively.

48. The construction system of claim 38 wherein the length and height of the stud brackets is about the height of the floor joist and about twelve inches, respectively.

49. The construction system of claim 38 wherein the units in which the scoring marks on the peak bracket are calibrated are degrees.

50. The construction system of claim 38 wherein the units in which the scoring marks on the peak bracket are calibrated are roof pitch.

51. The construction system of claim 38 wherein the predetermined number of holes in the spine of the peak bracket, the channel bracket, the slot brackets, the compression brackets, the truss brackets, and the stud brackets is one per said steel member adjacent the spine.

52. The construction system of claim 38 wherein the predetermined number of holes in the spine of the peak bracket, the channel bracket, the slot brackets, the compression brackets, the truss brackets, and the stud brackets is two per said steel member adjacent the spine.

53. The construction system of claim 38 wherein the predetermined number of holes in the spine of the peak bracket, the channel bracket, the slot brackets, the compression brackets, the truss brackets, and the stud brackets is four per said steel member adjacent the spine.

54. The construction system of claim 38 wherein the steel members further comprise C channel.

55. A construction system for building a steel frame using steel members, comprising:

rafters formed of the steel members for forming a roof portion of the steel frame, the rafters having slots, a ceiling joist having two ends and formed of the steel members for forming a ceiling portion of the steel frame, the ceiling joist having slots, compression webs formed of the steel members, the compression webs disposed between the rafters and the ceiling joists, for distributing load between the rafters and the ceiling joists, the compression webs fitting into the slots in the rafters and the ceiling joist, tension webs formed of the steel members, the tension webs disposed between the rafters, the ceiling joists, and the compression webs, for inhibiting distortion of the roof, the tension webs fitting into the slots in the rafters and the ceiling joist, a unitary peak bracket connecting two of the rafters at a variable roof pitch to one of the compression webs, the peak bracket connected to three outside surfaces on each of the two rafters and on two outside surfaces of the compression web, each of the two connected rafters thereby having a connected end and an unconnected end, the peak bracket having a length, width, and height, and also having a spine with four overlapping flaps adjacent the spine, the four flaps disposed at ninety degree angles from the spine, such that the four flaps and the spine have a cross-section generally resembling a U shape, the spine bendable to a variable degree at a position between the four flaps, at least one of the four flaps having alignment means on it, the alignment means calibrated in units that indicate the variable degree at which the spine is bent, the spine having a predetermined number of holes in it, and each flap having at least eight holes in it, the eight holes in each flap disposed such that four holes in each flap align with the compression web and one of the two connected rafters, and eave brackets connecting the two unconnected ends of the two connected rafters to the ends of the ceiling joist, such that the ends of the ceiling joist align with the unconnected ends of the two connected rafters, the eave brackets having a length, width, and height, and also having a spine with four flaps adjacent the spine, the four flaps disposed at ninety degree angles from the spine, such that the four flaps and the spine have a cross-section generally resembling a U shape, the spine bendable to a variable degree at a position between the four flaps, at least one of the four flaps having alignment means on it, the alignment means calibrated in units that indicate the variable degree at which the spine is bent, the spine having a predetermined number of holes in it, and each flap having at least four holes in it, the four holes in each flap disposed such that the four holes in each flap align with one of the ceiling joist and one of the two connected rafters.

56. The construction system of claim 55 wherein the compression webs and tension webs further comprise box channel.

57. The construction system of claim 55 wherein the rafters and the ceiling joist further comprise c channel.

* * * * *